United States Patent
Miyashita et al.

(10) Patent No.: US 11,090,310 B2
(45) Date of Patent: Aug. 17, 2021

(54) METHODS AND COMPOSITIONS FOR TREATING HYPERTRIGLYCERIDEMIA

(71) Applicants: THE REGENTS OF THE UNIVERSITY OF CALIFORNIA, Oakland, CA (US); GUNMA UNIVERSITY, Gunma (JP); Kazuya Miyashita, Gunma (JP)

(72) Inventors: Kazuya Miyashita, Gunma (JP); Stephen G. Young, Los Angeles, CA (US); Anne P. Beigneux, Los Angeles, CA (US); Loren G. Fong, Los Angeles, CA (US); Katsuyuki Nakajima, Gunma (JP)

(73) Assignee: The Regents of the University of California, Oakland, CA (US)

( * ) Notice: Subject to any disclaimer, the term of this patent is extended or adjusted under 35 U.S.C. 154(b) by 150 days.

(21) Appl. No.: 16/320,899

(22) PCT Filed: Jul. 28, 2017

(86) PCT No.: PCT/IB2017/054618
§ 371 (c)(1),
(2) Date: Jan. 25, 2019

(87) PCT Pub. No.: WO2018/020477
PCT Pub. Date: Feb. 1, 2018

(65) Prior Publication Data
US 2019/0160076 A1 May 30, 2019

Related U.S. Application Data

(60) Provisional application No. 62/367,881, filed on Jul. 28, 2016.

(51) Int. Cl.
| | |
|---|---|
| *G01N 33/536* | (2006.01) |
| *A61K 31/557* | (2006.01) |
| *G01N 33/68* | (2006.01) |
| *G01N 33/92* | (2006.01) |
| *C07K 16/28* | (2006.01) |
| *A61P 3/06* | (2006.01) |
| *C12N 15/63* | (2006.01) |
| *G01N 33/577* | (2006.01) |
| *A61M 1/34* | (2006.01) |

(52) U.S. Cl.
CPC ............. *A61K 31/557* (2013.01); *A61P 3/06* (2018.01); *C07K 16/28* (2013.01); *C12N 15/63* (2013.01); *G01N 33/577* (2013.01); *G01N 33/6854* (2013.01); *G01N 33/92* (2013.01); *A61M 1/3496* (2013.01); *C07K 2317/21* (2013.01); *C07K 2317/76* (2013.01); *G01N 2800/044* (2013.01)

(58) Field of Classification Search
None
See application file for complete search history.

(56) References Cited

U.S. PATENT DOCUMENTS

| | | |
|---|---|---|
| 2014/0050668 A1 | 2/2014 | Bruns et al. |
| 2014/0134262 A1 | 5/2014 | Arai et al. |
| 2014/0357717 A1 | 12/2014 | Braeckman et al. |

FOREIGN PATENT DOCUMENTS

| | | |
|---|---|---|
| CN | 100422743 | 10/2008 |

OTHER PUBLICATIONS

Gin et al., The Acidic Domain of GPIHBP1 is important for the Binding of Lipoprotein Lipase and Chylomicrons, Journal of Biological Chemistery, vol. 283, No. 43, Oct. 2008, pp. 29554-26562. (Year: 2008).*
Chiu et al., Endothelial cells respond to hyperglycemia by increasing the LPL transporter GPIHBP1, Am J Physiol Endocrinol Metab 306: E1274-E1283, 2014. (Year: 2014).*
Miyashita et al., An ELISA for quantifying GPIHBP1 autoantibodies and making a diagnosis of the GPIHBP1 autoantibody syndrome, Clinica Chimica Acta, 487, 2018, pp. 174-178. (Year: 2018).*
Beigneux et al., "Assessing the role of the glycosylphosphatidylinositol-anchored high density lipoprotein-binding protein 1 (GPIHBP1) three-finger domain in binding lipoprotein lipase" *J. Biol Chem.*, 2011, 286:19735-19743.
Beigneux et al., "Autoantibodies Against GPIHBP1 as a Cause of Hypdertiglyceridemia" *The New England Journal of Medicine*, 2017, 376(17):1647-1658.
Beigneux et al., "Glycosylphosphatidylinositol-anchored high density lipoprotein 1 plays a critical role in the lipolytic processing of chylomicrons" *Cell Metab.*, 2007, 5:279-291.
Beigneux et al., "GPIHBP1 missense mutations often cause multimerization of GPIHBP1 and thereby prevent Lipoprotein Lipase binding" *Circ. Res.*, 2014, 116:624-632.
Davies et al., "GPIHBP1 is responsible for the entry of lipoprotein lipase into capillaries" *Cell Metab*, 2010, 12:42-52.
Franssen et al., "Chylomicronemia with low postheparin lipoprotein lipase levels in the setting of GPIHBP1 defects" *Circ. Cardiovasc. Genet.*, 2010, 3:169-178.
Hu et al., "Monoclonal antibodies that bind to the Ly6 domain of GPIHBP1 abolish the binding of LPL" *J. Lipid Res.*, 2017, 58:208-215.

(Continued)

*Primary Examiner* — Gary Counts
(74) *Attorney, Agent, or Firm* — Norton Rose Fulbright US LLP

(57) ABSTRACT

This application describes novel therapeutic strategies for treating patients with hypertriglyceridemia and/or chylomicronemia based on the presence of GPIHBP1 autoantibodies. It was unexpectedly found that autoantibodies to GPIHBP1, a GPI anchored protein of capillary endothelial cells that shuttles lipoprotein lipase to its site of action in the capillary lumen, were found to be present in patients with hypertriglyceridemia, and that the autoantibodies blocked the binding of lipoprotein lipase (LPL) to GPIHBP1. Patients having hypertriglyceridemia and/or chylomicronemia and also having GPIHBP1 autoantibodies may be treated with a therapeutically effective amount of an immunosuppressive treatment and/or GPIHBP1 activator.

13 Claims, 13 Drawing Sheets
Specification includes a Sequence Listing.

(56) References Cited

OTHER PUBLICATIONS

International Search Report and Written Opinion issued in International Patent Application No. PCT/IB2017/054618, dated Dec. 22, 2017.
Machida et al., "Determination turbidimetric immunoassay of serum lipoprotein lipase using a latex particle-enhanced automated analyzer" *Clin. Chim Acta.*, 2015, 442:130-135.
Young et al., "Two new monoclonal antibody-based enzyme-linked assays ofapolipoprotein B." *Clin. Chem.*, 1986, 32:1484-1490.

* cited by examiner

A  Screening for GPIHBP1 autoantibodies

B  Specificity of autoantibodies on western blot analysis

METHODS AND COMPOSITIONS FOR TREATING HYPERTRIGLYCERIDEMIA

CROSS-REFERENCE TO RELATED APPLICATIONS

This application is a national phase application under 35 U.S.C. § 371 of International Application No. PCT/IB2017/054618 filed Jul. 28, 2017, which claims benefit to U.S. Provisional Patent Application No. 62/367,881, filed Jul. 28, 2016. The entire contents of the referenced applications are incorporated herein by reference.

STATEMENT REGARDING FEDERALLY-SPONSORED RESEARCH

This invention was made with government support under Grant Nos. R01HL087228 and P01HL090553 awarded by the National Heart, Lung, and Blood Institute (NHLBI), National Institutes of Health (NIH). The government has certain rights in the invention.

BACKGROUND

1. Field of the Invention

The present invention relates generally to the field of medicine. More particularly, it concerns methods and compositions involving treatment of hypertriglyceridemia.

2. Background

Hypertriglyceridemia is a condition in which triglyceride levels are elevated, often caused or exacerbated by uncontrolled diabetes mellitus, obesity, and sedentary habits. In certain circumstances, the underlying cause of hypertriglyceridemia is unknown and traditional treatments, such as lifestyle modulation or pharmacological therapies are ineffective. There is a need in the art for a more detailed understanding of the etiology of hypertriglyceridemia and more effective therapies in cases for which traditional therapies are ineffective.

SUMMARY OF THE DISCLOSURE

The current disclosure fulfills the need in the art by providing a novel therapeutic strategy for patients with hypertriglyceridemia and/or chylomicronemia, wherein the patient is determined to have autoantibodies to GPIHBP1. It was unexpectedly found that autoantibodies to GPIHBP1, a GPI anchored protein of capillary endothelial cells that shuttles lipoprotein lipase to its site of action in the capillary lumen, were found to be present in patients with hypertriglyceridemia, and that the autoantibodies blocked the binding of lipoprotein lipase (LPL) to GPIHBP1. Accordingly, aspects of the disclosure relate to a method for treating hypertriglyceridemia and/or chylomicronemia in a patient comprising administering a therapeutically effective amount of an immunosuppressive treatment and/or GPIHBP1 activator to the patient; wherein the patient has been determined to have GPIHBP1 autoantibodies.

Further aspects relate to a method for classifying a subject or a method for detecting GP1HBP1 autoantibodies in a subject, the method comprising: a. obtaining a sample from the subject; and b. detecting the presence or absence of GP1HBP1 autoantibodies in the sample from the subject.

Further aspects relate to a method for diagnosing a subject, the method comprising: detecting the presence or absence of GP1HBP1 autoantibodies in a biological sample from the subject; and diagnosing the subject with GP1HBP1 autoantibody-induced hypertriglyceridemia when the presence of GP1HBP1 autoantibodies are detected.

Further aspects relate to a method for treating GP1HBP1 autoantibody-induced hypertriglyceridemia in a patient in need thereof, the method comprising administering a therapeutically effective amount of an immunosuppressive treatment and/or GPIHBP1 activator to the patient. In some embodiments, the patient has been determined to have GP1HBP1 autoantibodies.

In some embodiments of the above-disclosed aspects, the method further comprises obtaining a sample from the subject. In some embodiments, the method further comprises treating the subject diagnosed with GP1HBP1 autoantibody-induced hypertriglyceridemia with an immunosuppressive treatment and/or GPIHBP1 activator.

In some embodiments, detecting the presence or absence of GP1HBP1 autoantibodies comprises an ELISA assay. In some embodiments, detecting the presence or absence of GP1HBP1 autoantibodies comprises an assay described herein. In some embodiments, detecting GPIHBP1 autoantibodies comprises detecting the binding between antibodies isolated from a sample from the patient and GPIHBP1.

In some embodiments of the above-disclosed methods, the protein level or detected protein level of GP1HBP1 is greater than or less than 200 pg/mL. In some embodiments, the protein level or detected protein level of GP1HBP1 is greater than or less than 25, 75, 50, 100, 125, 150, 175, 200, 225, 250, 275, 300, 325, 350, 375, or 400 pg/mL (or any derivable range therein). In some embodiments, the detected autoantibodies comprise autoantibodies that bind specifically to monomeric non-reduced GPIHBP1.

In some embodiments, the method further comprises isolating GP1HBP1 autoantibodies from the subject. In some embodiments, the method further comprises detecting the binding of LPL to GP1HBP1 in the presence of the autoantibodies. In some embodiments, detecting the presence or absence of GP1HBP1 autoantibodies in the sample from the subject comprises contacting the sample from the subject with GP1HBP1 and detecting the binding between antibodies in the sample from the subject and GP1HBP1. In some embodiments, the method further comprises contacting the sample with LPL and detecting the binding between LPL and GP1HBP1 in the presence of the sample from the subject.

In some embodiments, the subject has chylomicronemia. In specific embodiments, the subject has symptoms of chylomicronemia, is at risk for chylomicronemia, has been diagnosed with chylomicronemia, and/or is being treated for chylomicronemia. In some embodiments, the expression levels of LPL and/or GPIHBP1 are determined to be normal based on comparing to control level.

In some embodiments, an immunosuppressive treatment is administered to the patient. In some embodiments, the immunosuppressive treatment is one that reduces autoantibodies in the patient. In some embodiments, the immunosuppressive treatment comprises belimumab, rituximab, plasmapheresis, WIG, Protein A-based absorbents, Anti-IL-6R, Anti-CD20, Anti-BLyS, BR3-Ig, AMG 623, Anti-BR3, TACI-Ig, Anti-CD22, LTbetaR-Ig, Anti-interferon-alpha, Anti-CD40, and Anti-CD40L, antithymocyte globulin, muromonab-CD3, and alemtuzumab. In some embodiments, the immunosuppressive treatment is one known in the art or described herein. In some embodiments, the immunosuppressive treatment comprises plasmapheresis.

In some embodiments, a GPIHBP1 activator is administered to the patient. In some embodiments, the GPIHBP1 activator is a GPIHBP1 polypeptide. In some embodiments, the GPIHBP1 polypeptide binds to the autoantibodies in the patient.

In some embodiments, the method further comprises detecting GPIHBP1 autoantibodies in the patient. In some embodiments, the autoantibodies are detected by ELISA. In some embodiments, the autoantibodies are detected by methods known in the art or described herein. In some embodiments, detecting GPIHBP1 autoantibodies comprises detecting the binding between antibodies isolated from a sample from the patient and GPIHBP1. In some embodiments, the GPIHBP1 is recombinant. In some embodiments, the recombinant GPIHBP1 comprises an amino acid sequence with at least 80% identity to SEQ ID NO:4. In some embodiments, the recombinant GPIHBP1 comprises an amino acid sequence with at least 70%, 80%, 85%, 90%, 95%, 96%, 97%, 98%, or 99% (or any derivable range therein) identity to SEQ ID NO:4. In some embodiments, the recombinant GPIHBP1 is produced in insect cells. In some embodiments, the insect cells are *Drosophila melanogaster*. In some embodiments, the GPIHBP1 is monomeric non-reduced GPIHBP1.

In some embodiments, the patient or subject has been diagnosed with hypertriglyceridemia. In specific embodiments, the subject has symptoms of hypertriglyceridemia, is at risk for hypertriglyceridemia, has been diagnosed with hypertriglyceridemia, and/or is being treated for hypertriglyceridemia. In some embodiments, the patient has been previously treated for hypertriglyceridemia. In some embodiments, the patient was non-responsive to the previous treatment. In some embodiments, the patient does not have diabetes or coronary artery disease. In some embodiments, the patient is not obese. In some embodiments, the patient is not genetically deficient for GPIHBP1. In some embodiments, the expression level and/or activity level of GPIHBP1 and/or LPL in a biological sample from the patient is normal or reduced compared to a control. In some embodiments, the control is the level of GPIHBP1 in a biological sample from a patient without hypertriglyceridemia. In some embodiments, the control may be the level of a protein, antibody, or nucleic acid in a biological sample with a patient known to have GP1HBP1 autoantibodies and also, optionally, known to have hypertriglyderidemia and/or chylomicronemia. One skilled in the art would understand that, when comparing to a sample known to have GP1HBP1 autoantibodies, the level of the tested substance would be expected to be similar or within 0.5, 1, 1.5, or 2 standard deviations. In some embodiments the biological sample from the patient or control comprises capillary endothelial cells, serum, whole blood, or extracts or fractions thereof. In some embodiments, the biological sample is one described herein. In some embodiments, the hypertriglyceridemia is of unknown etiology.

In some embodiments, the autoantibodies bind only to monomeric non-reduced GPIHBP1. In some embodiments, the antibodies have been determined to bind only to monomeric non-reduced GPIHBP1. In some embodiments, the autoantibodies have been determined to inhibit the binding of LPL to GPIHBP1.

In some embodiments, the method further comprises isolating GPIHBP1 autoantibodies from the patient. In some embodiments, the isolated autoantibodies are determined to inhibit the binding of LPL to GPIHBP1.

In some embodiments, the patient is one that has been determined to have low levels of LPL in a sample from the patient compared to a control. In some embodiments, the method further comprises detecting the level of LPL in a sample from the patient. In some embodiments, the level of LPL is reduced by at least 10, 15, 20, 25, 30, 35, 40, 45, 50, 55, 60, 65, 70, 75, 80, 85, 90, 95, 96, 97, 98, 99, or 100% (or any range derivable therein) compared to the control. In some embodiments, the LPL is reduced in pre-heparin plasma. In some embodiments, diagnosing the subject with GP1HBP1 autoantibody-induced hypertriglyceridemia further comprises diagnosing the subject with GP1HBP1 autoantibody-induced hypertriglyceridemia when the detected LPL level is less than 50 ng/mL. In some embodiments, diagnosing the subject with GP1HBP1 autoantibody-induced hypertriglyceridemia further comprises diagnosing the subject with GP1HBP1 autoantibody-induced hypertriglyceridemia when the detected LPL level is less than 200, 175, 150, 125, 100, 75, 50, 40, 30, 20, 10, or 5 ng/mL (or any derivable range therein).

The inhibition of binding may be at least, at most, or exactly 5, 10, 15, 20, 25, 30, 35, 40, 45, 50, 55, 60, 65, 70, 75, 80, 85, 90, 95, 96, 97, 98, 99, or 100% inhibition (or any range derivable therein).

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene or protein encoding GPIHBP1 or LPL or a signal intensity or level corresponding to antibody/antigen binding in an immunology assay with a sample from a patient; and b) determining a difference value in the expression or activity levels using the information corresponding to the expression or activity levels in the sample compared to a control or reference expression or activity level for the gene or quantifying the signal intensity to determine whether specific binding has occurred.

In some embodiments, receiving information comprises receiving from a tangible data storage device information corresponding to the expression or activity levels or signal intensities from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a therapy if the patient is determined to have GPIHBP1 autoantibodies.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows western blots demonstrating GPIHBP1 autoantibodies in plasma samples 38 and 101. Proteins in the medium of GPIHBP1-transfected Drosophila S2 cells were size-fractioned by SDS-PAGE under reducing and nonreducing conditions. GPIHBP1 contains a tightly folded cysteine-rich domain (Ly6 domain) that is essential for binding LPL. It was reasoned that some of the autoantibodies might bind to GPIHBP1's Ly6 domain and that disrupting the disulfide bonds with reducing reagents might disrupt the epitope of some of the autoantibodies. The autoantibodies in plasma 101 (level, 20 AU GPIHBP1 autoantibodies/ml) bound to both reduced (R) and nonreduced GPIHBP1; additional nonspecific binding was seen under reducing conditions. The autoantibodies in plasma 38 (level, 20 AU GPIHBP1 autoantibodies/ml) bound avidly only to nonreduced (NR) GPIHBP1. The lower panels show the same blots incubated with the GPIHBP1-specific monoclonal antibody RF4 (4 µg/ml). The monoclonal antibody RF4 binds to the acidic domain of GPIHBP1 and therefore binds reduced and nonreduced human GPIHBP1; it also binds to GPIHBP1 dimers and multimers (GPIHBP1 multimers occur in the setting of insect cell overexpression and are due to inappropriate intermolecular disulfide bonds). C, negative control (culture medium from S2 cells that do not express human GPIHBP1). FIG. 2B shows an immunocytochemistry experiment documenting that GPIHBP1 autoantibodies in plasma sample 38 (1:20 dilution; third column) bound to cells that had been transfected with an S-protein-tagged version of human GPIHBP1; they did not bind to non-transfected cells or to cells that were transfected with S-protein-tagged human CD59. CD59- and GPIHBP1-transfected cells were detected with an antibody against the S-protein tag (first column); GPIHBP1-expressing cells were also detected with a GPIHBP1-specific monoclonal antibody RG3 (second column). DNA was stained with DAPI to reveal all cells (both transfected and non-transfected) on the coverslip (fourth column. The immunoglobulins in plasma 3 (from a patient homozygous for a deletion of GPIHBP1) did not bind to GPIHBP1-transfected cells.

FIG. 4A shows a western blot of cell extracts from CHO cells that had been transfected with S-protein-tagged wild-type GPIHBP1 (GPIHBP1-wt) or a mutant GPIHBP1 (GPIHBP1-W109S), which lacks the ability to bind LPL. The LPL used in these experiments was V5-tagged. Western blots were performed with a goat antibody against the S-protein tag (Abcam, 5 µg/ml), followed by an IRDye 680-donkey anti-goat IgG (LI_COR, 1:2000; GPIHBP1) and an IRDye 800-V5 antibody (1:500; LPL). Actin was used as a loading control, and was detected with a rabbit antibody against actin (Abcam, 5 µg/ml) followed by an IRDye 800-donkey anti-rabbit IgG (LI-COR, 1:2000; lower panel). In lane 3, LPL binding to GPIHBP1-wt is demonstrated. In lane 4, control plasma 3 did not block binding of LPL to GPIHBP1-wt. In lane 5, pre-incubation of cells with plasma 38 (1:20) abolished LPL binding. In lane 6, the GPIHBP1-specific monoclonal antibody RG3 (20 µg/ml) also blocked the binding of LPL to GPIHBP1-wt. In lane 2, a mutant GPIHBP1 (GPIHBP1-W109S), which lacks the ability to bind LPL, was included as a control. FIG. 4B shows an immunocytochemistry study revealing that the binding of immunoglobulins (third column) in plasma samples 102 and 111 blocked the binding of LPL (second column) to GPIHBP1-expressing cells (first column). Under the same conditions, the immunoglobulins in control plasma 3 did not block binding of LPL to GPIHBP1-transfected cells. Cells expressing GPIHBP1-W109S did not bind LPL. DNA was stained with DAPI (fourth column).

DESCRIPTION OF ILLUSTRATIVE EMBODIMENTS

Figure 1:
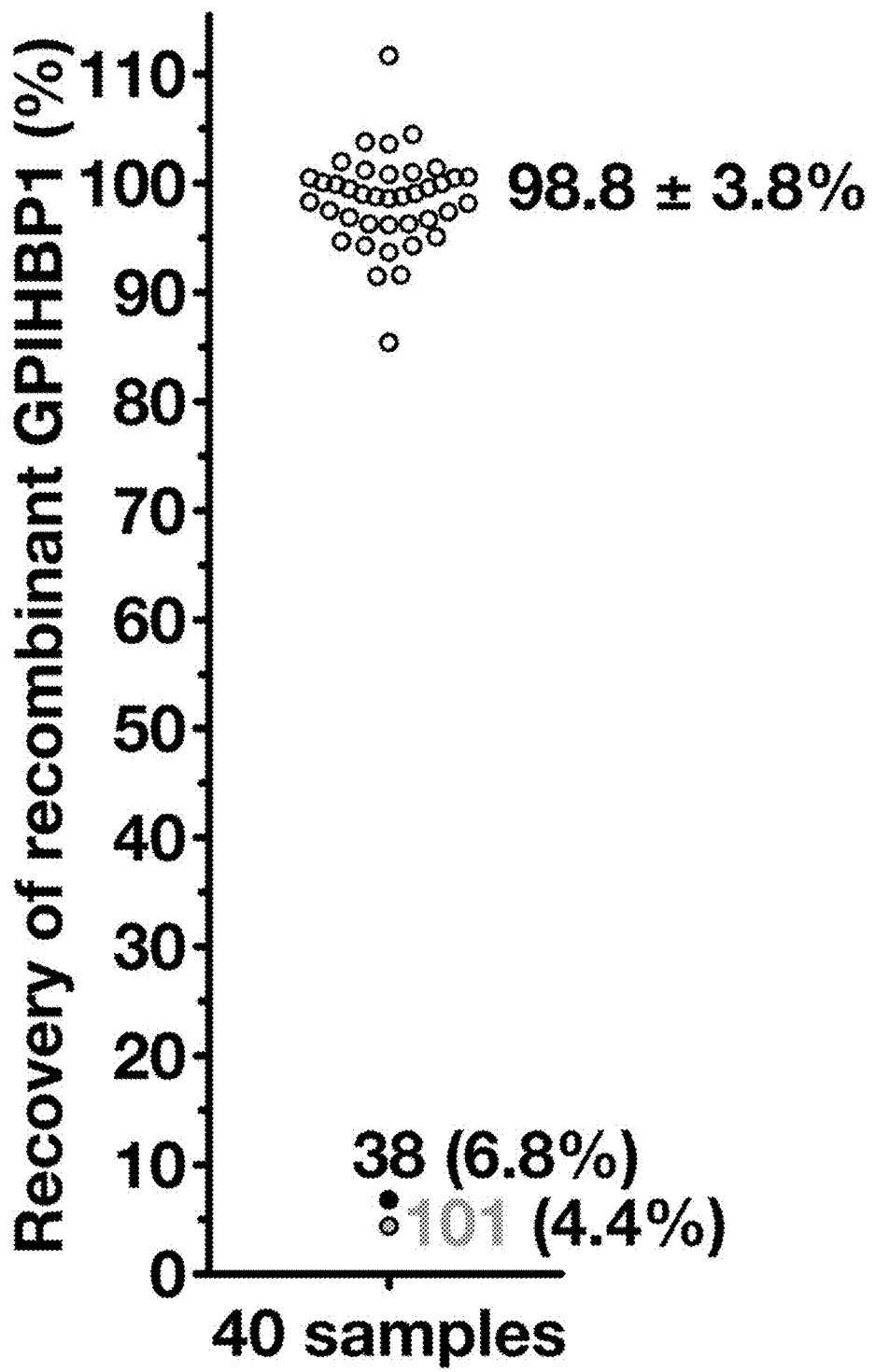
FIG. 1. GPIHBP1 Immunoassay Interference. Recovery of spiked recombinant human GPIHBP1 (rhGPIHBP1) in a monoclonal antibody-based ELISA. GPIHBP1 levels in 1:20 dilutions of plasma were measured before and after spiking the sample with 62.5 pg of rhGPIHBP1. In 38 of 40 plasma samples, the recovery of spiked rhGPIHBP1 was nearly complete (98.8±3.8%). In these samples, the mean GPIHBP1 values were 21±3 pg/ml before "spiking" with rhGPIHBP1, and 82.5±3 pg/ml after spiking with the rhGPIHBP1. The recovery of rhGPIHBP1 in samples 38 and 101 was very low (6.8% and 4.4%, respectively). The GPIHBP1 level in the 1:20 dilution of plasma 38 was 3 pg/ml and was 4.5 pg/ml after spiking the sample. The GPIHBP1 level in the 1:20 dilution of plasma 101 was 1 pg/ml and was 3 pg/ml after spiking.
Figure 2A:
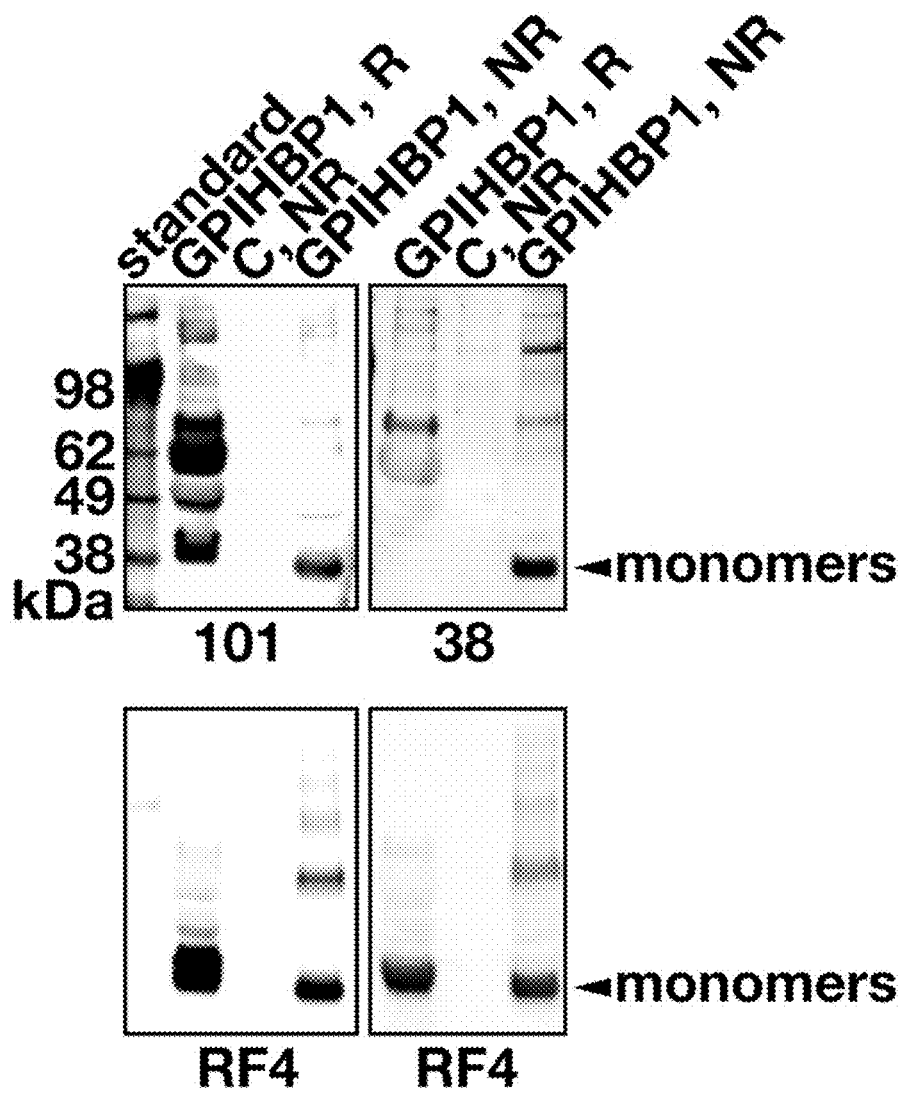
FIG. 2A-B. GPIHBP1 Autoantibodies in Plasma Samples 38 and 101.
Figure 2B:
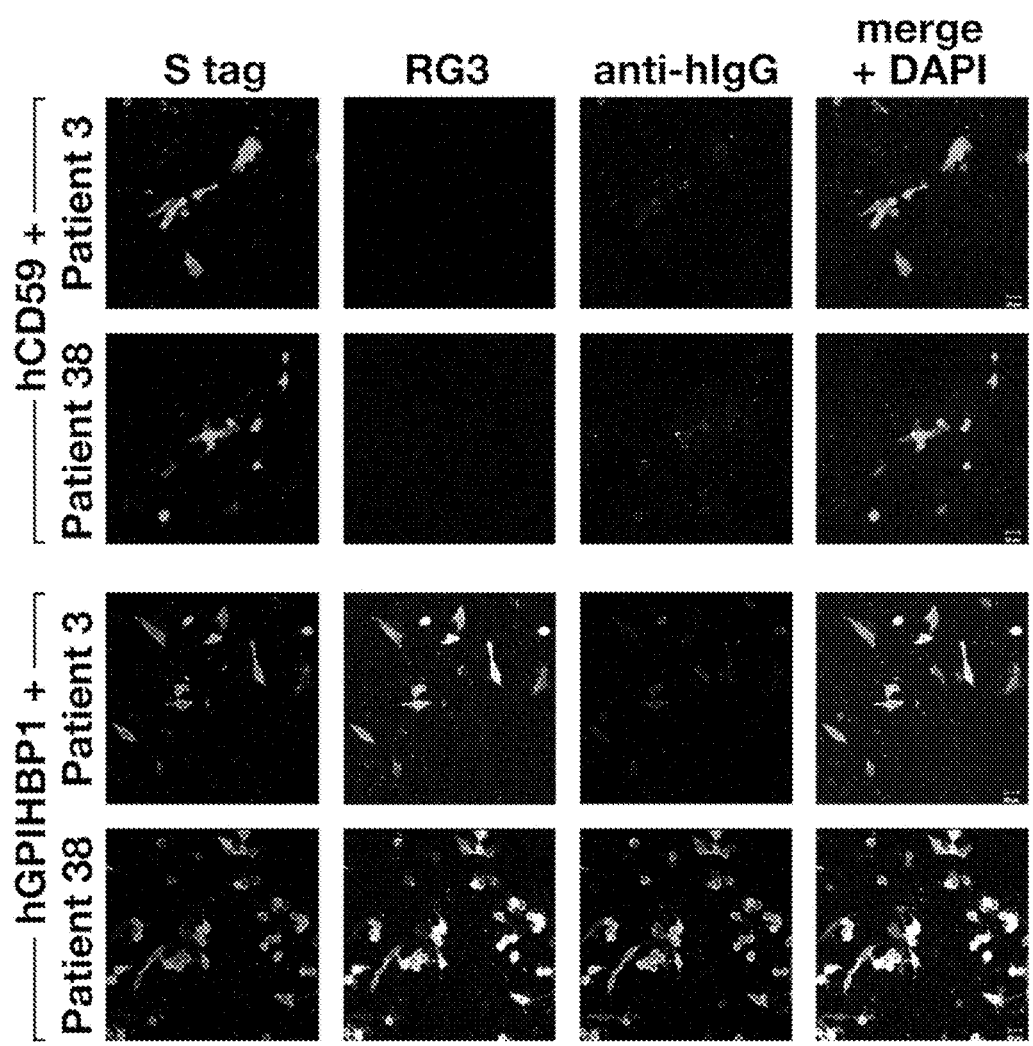
Figure 4A:
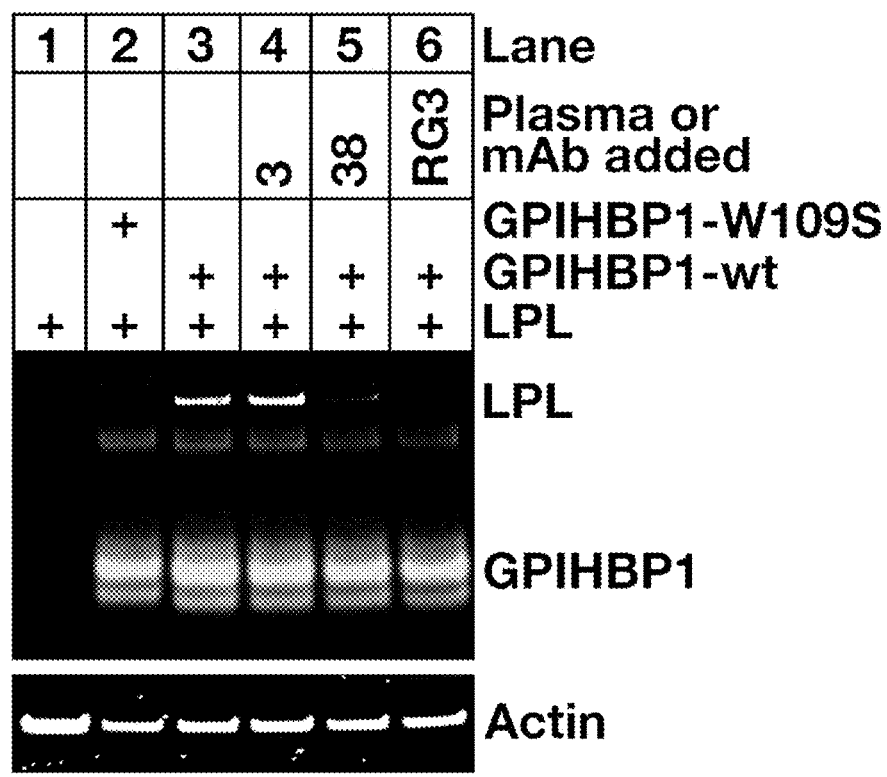
FIG. 4A-B. GPIHBP1 Autoantibodies Block the Binding of LPL to GPIHBP1.
Figure 4B:
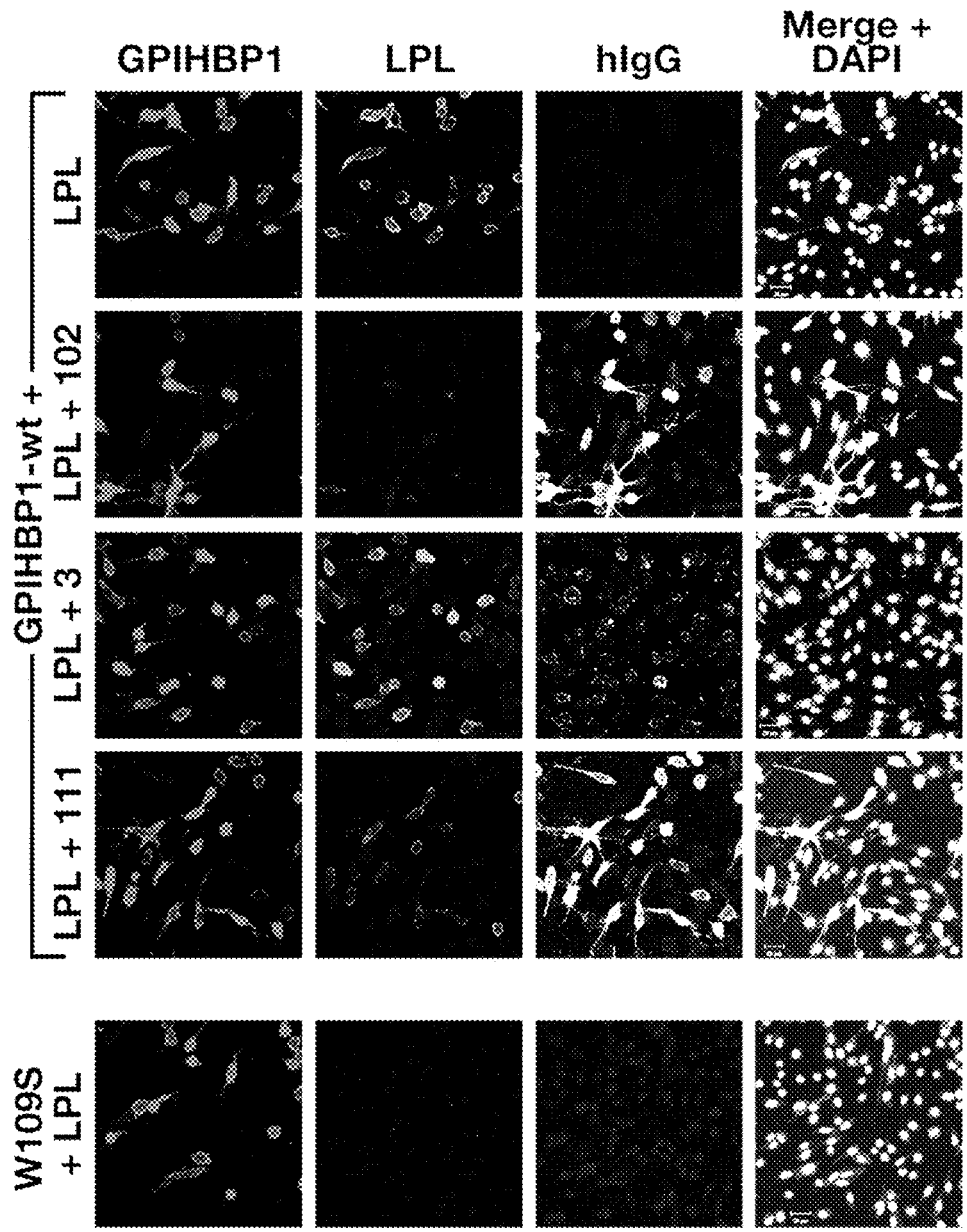
Figure 5:
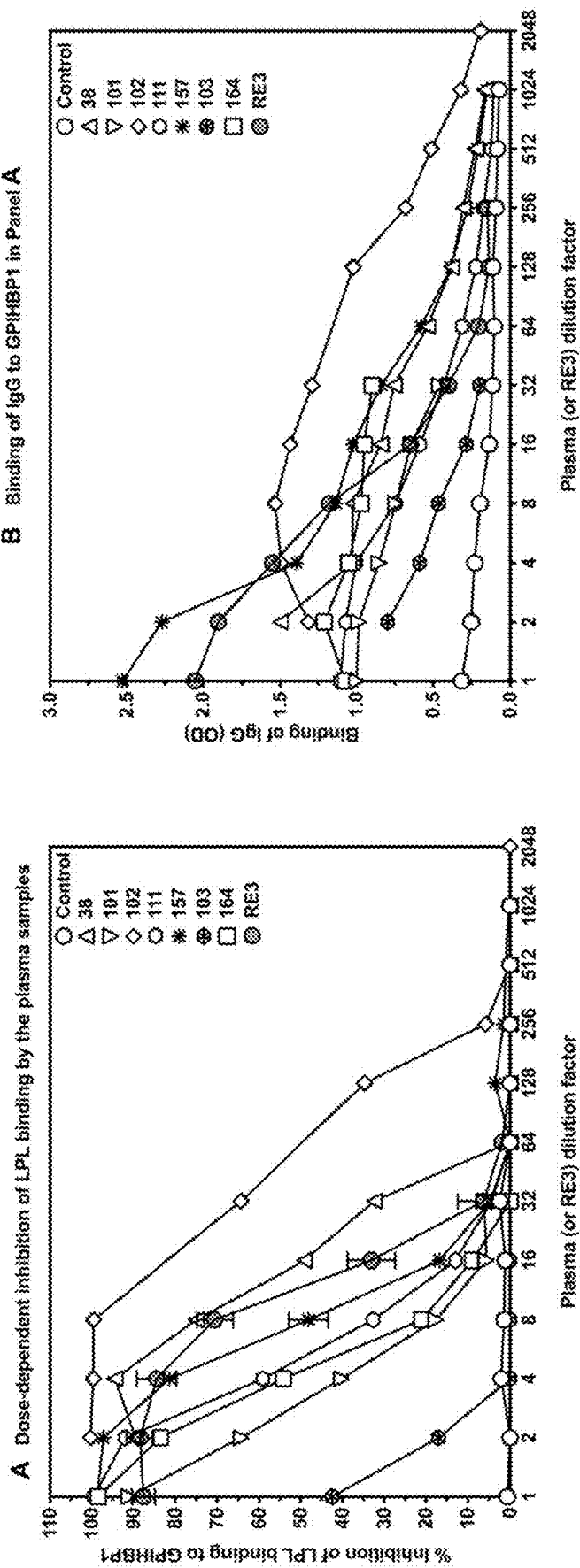
FIG. 5. GPIHBP1 Autoantibodies Block LPL Binding to GPIHBP1 in a Dose-dependent Manner. Panel (A) shows results of a solid-phase assay of LPL binding to GPIHBP1. Briefly, ELISA plates were coated with the monoclonal antibody R24 and incubated with uPAR-tagged human GPIHBP1, followed by an overnight incubation with serial dilutions of human plasma samples or the GPIHBP1-specific monoclonal antibody RE3. The next day, after incubating the plates with V5-tagged human LPL, the amount of GPIHBP1-bound LPL was detected with an HRP-labeled V5 antibody, and compared to the amount of bound LPL in the absence of human plasma or monoclonal antibody RE3 (set at 100% binding). These ELISA studies showed that GPIHBP1 autoantibodies in the plasma of six adult subjects with chylomicronemia (38, 101, 102, 111, 157, 164) and the plasma of infant 103 blocked binding of LPL to GPIHBP1. The monoclonal antibody RE3 also blocked binding of LPL to GPIHBP1 (the 1:1 dilution for mAb RE3 corresponds to 20 μg/ml). A control plasma sample had no capacity to block LPL binding to GPIHBP1. Panel (B) shows the amount of IgG binding to GPIHBP1 for each of the dilutions tested in Panel (A). Plasma samples 102, 38 and 157 had the highest GPIHBP1 autoantibody titers.

It was unexpectedly found that autoantibodies to GPIHBP1, a GPI anchored protein of capillary endothelial cells that shuttles lipoprotein lipase to its site of action in the capillary lumen, were found to be present in patients with hypertriglyceridemia, and that the autoantibodies blocked the binding of LPL to GPIHBP1 (FIG. 1). Immunoassays such as western blots, showed that the autoantibodies bound specifically to recombinant GPIHBP1 and did so in a characteristic fashion for antibodies against Ly6 proteins (binding only to the monomeric nonreduced version of the protein—FIG. 2A, FIG. 3(B)). The autoantibodies also bound specifically to GPIHBP1 expressed on the surface of GPIHBP1-transfected cells (FIG. 2B); they did not bind to CD59 (another member of the Ly6 family) on CD59-transfected cells (FIG. 2B). Most importantly, the autoantibodies blocked the binding of LPL to GPIHBP1 in both cell-free and cell-based assays (FIG. 4A-B, FIG. 5).

Figure 6:
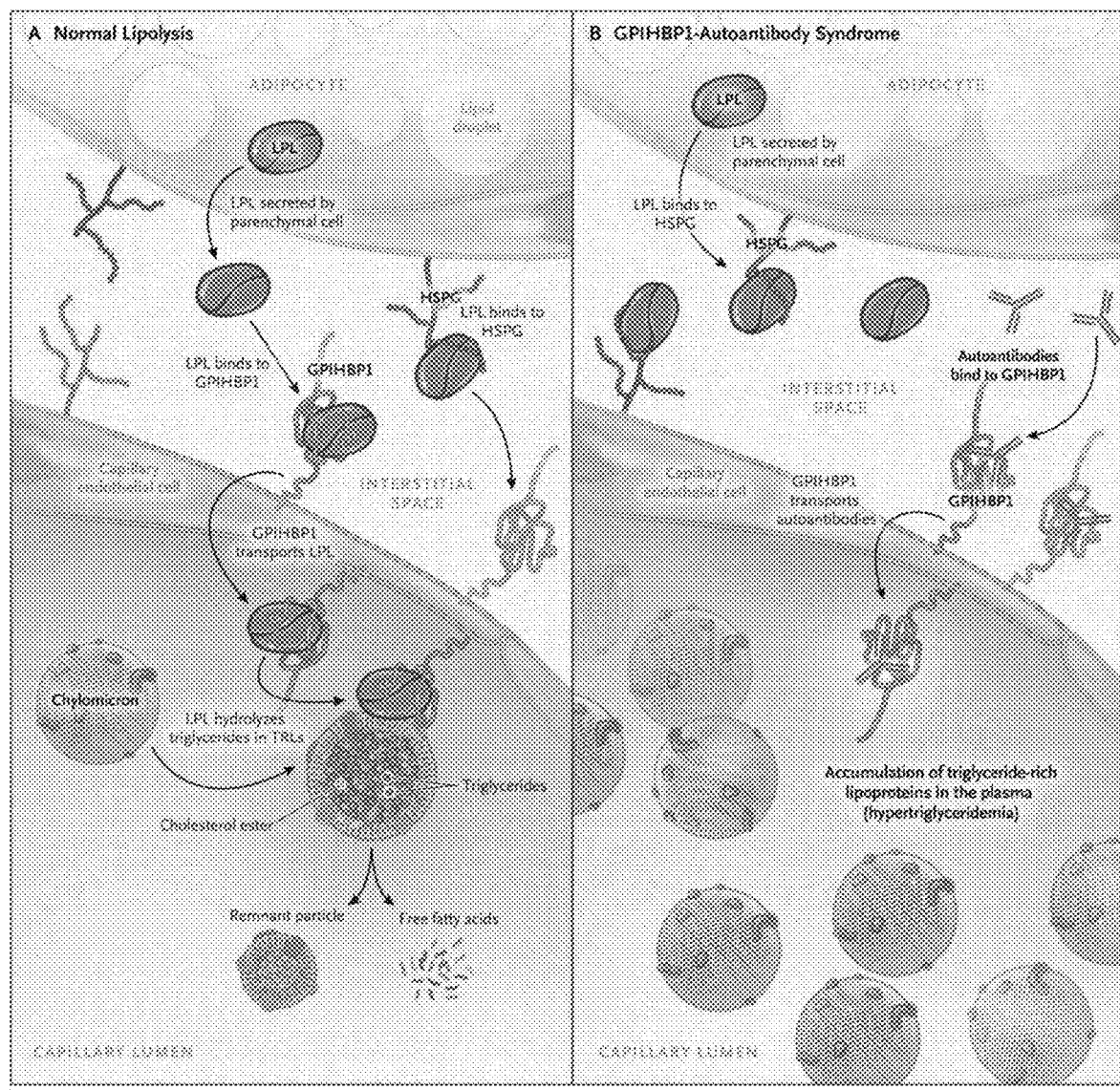
FIG. 6. Normal Lipolysis and Defective Triglyceride Processing in the GPIHBP1-Autoantibody Syndrome. Panel (A) shows normal intravascular processing of triglycerides in a healthy person, and Panel B) shows defective triglyceride processing in a patient with the GPIHBP1-autoantibody syndrome. Normally, the lipoprotein lipase that is secreted by parenchymal cells (e.g., adipocytes and myocytes) is captured by GPIHBP1 on the basolateral surface of endothelial cells. GPIHBP1 then transports lipoprotein lipase across endothelial cells to the capillary lumen, where the lipoprotein lipase hydrolyzes triglycerides in triglyceride-rich lipoproteins (e.g., very-low-density lipoproteins and chylomicrons). GPIHBP1 autoantibodies block the binding of lipoprotein lipase to GPIHBP1 and therefore block the transport of lipoprotein lipase to the capillary lumen, resulting in an accumulation of triglyceride-rich lipoproteins in the plasma (hypertriglyceridemia). HSPG denotes heparan sulfate proteoglycan, and TRL triglyceride-rich lipoprotein.

Patients that have been determined to have the GPIHBP1 autoantibodies had low levels of LPL in their plasma (Table 1), a consequence of defective GPIHBP1-mediated transport of LPL to the capillary lumen (FIG. 6). The current invention is significant, since it presents a novel therapy for this disease and provides a new treatment for hypertriglyceridemia, including hypertriglyceridemia of unknown etiology.

I. Definitions

As used herein, the term "antibody" encompasses antibodies and antibody fragments thereof, derived from any antibody-producing mammal (e.g., mouse, rat, rabbit, and primate including human), that specifically bind to GPIHBP1 polypeptides or portions thereof. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof. "Autoantibodies" refer specifically to antibodies produced by the immune system of an individual that are directed against one or more of the individual's own proteins.

Chylomicronemia refers to a disorder in which the body does not break down fats (lipids) correctly. This causes fat particles called chylomicrons to build up in the blood.

As used herein, the term "antibody fragment" refers to a portion derived from or related to a full-length anti-GPIHBP1 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the VH and VL domains of an antibody, wherein these domains are present in a single polypeptide chain. Generally, the Fv polypeptide further comprises a polypeptide linker between the VH and VL domains, which enables the scFv to form the desired structure for antigen binding.

The term substantially the same or not significantly different refers to a level of expression that is not significantly different than what it is compared to. Alternatively, or in conjunction, the term substantially the same refers to a level of expression that is less than 2, 1.5, or 1.25 fold different (or any range derivable therein) than the expression or activity level it is compared to.

The terms "subject" and "patient" are used interchangeably, and refer to any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately."

II. GPIHBP1

Glycosylphosphatidylinositol anchored high density lipoprotein binding protein 1 (GPI-HBP1) also known as high density lipoprotein-binding protein 1, GPI-HBP1, and HYPL1D is a protein that in humans is encoded by the GPIHBP1 gene.

Dietary fats are packaged by intestine into triglyceride-rich lipoproteins called chylomicrons. The triglycerides in chylomicrons are hydrolyzed by lipoprotein lipase (LPL) along the luminal surface of capillaries, mainly in heart, skeletal muscle, and adipose tissue. GPIHBP1 is a capillary endothelial cell protein that provides a platform for LPL-mediated processing of chylomicrons, and shuttles LPL to its site of action in the capillary lumen.

A representative protein sequence for GPIHBP1 comprises the following protein sequence: mkalgavlla lllfgrpgrg qtqqeeeeed edhgpddyde ededeveeee tnrlpggrsr vllrcytcks lprdercnit qncshgqtct tliahgntes glltthstwc tdscqpitkt vegtqvtmtc cqsslcnvpp wqssrvqdpt gkgaggprgs setvgaalll nllaglgamg arrp (SEQ ID NO:1).

A further representative sequence for GPIHBP1 comprises the following protein sequence:

(SEQ ID NO: 2)
MKALGAVLLA LLLFGRPGRG QTQQEEEEED EDHGPDDYDE
EDEDEVEEEE TNRLPGGRSR VLLRCYTCKS LPRDERCNLT
QNCSHGQTCT TLIAHGNTES GLLTTHSTWC TDSCQPITKT VEGTQ.

Variants and/or polypeptides with conservative amino acids are also contemplated. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

III. GPIHBP1 Activators and Immunosuppressive Therapies

In some embodiments, a GPIHBP1 activator is administered to the patient. In some embodiments, the activator comprises a GPIHBP1 polypeptide. In some embodiments, the GPIHBP1 polypeptide binds to autoantibodies in the subject, thereby reducing the amount of autoantibodies that can bind to GPIHBP1 and, in effect, acting as an indirect activator by interfering with autoantibody binding. In some embodiments, the GPIHBP1 activator increases the expression or protein activity of GPIHBP1 in the patient.

In some embodiments, an immunosuppressive therapy is administered to the patient. In some embodiments, the immunosuppressive therapy is one that reduces autoantibodies in the patient. Such immunosuppressive therapies are known in the art. For example, Belimumab has been shown to reduce autoantibodies (Stohl et al., *Arthritis Rheum.* 2012 July; 64(7):2328-37). Rituximab, by causing B-cell depletion, reducing the production of autoantibodies in patients (Mixalis L. Kosmidis, *Ther Adv Neurol Disord.* 2010 March; 3(2): 93-105). In some embodiments, the therapy that reduces autoantibodies is one that modulates B-cell function and/or comprises depleting antibodies against T cells, B cells, or both. In some embodiments, the immunosuppressive therapy that reduces autoantibodies in the subject comprises plasmapheresis.

In some embodiments, an immunosuppressive therapy is one that modulates B-cell function. Such agents include IVIG, Protein A-based absorbents, Anti-IL-6R, Anti-CD20, Anti-BLyS, BR3-Ig, AMG 623, Anti-BR3, TACI-Ig, Anti-CD22, LTbetaR-Ig, Anti-interferon-alpha, Anti-CD40, and/or Anti-CD40L. It is specifically contemplated that one or more of these agents may be excluded in some embodiments.

In some embodiments, the immunosuppressive therapy comprises depleting antibodies against T cells, B cells, or both. Exemplary therapeutics include a polyclonal antibody, horse or rabbit antithymocyte globulin, mouse monoclonal anti-CD3 antibody (muromonab-CD3), humanized monoclonal anti CD-52 antibody (alemtuzumab), and/or B-cell-depleting monoclonal anti-CD-20 antibody (rituximab). It is specifically contemplated that one or more of these therapeutics may be excluded in some embodiments.

In some embodiments, the immunosuppressive therapy comprises one known in the art or described herein such as plasmapheresis, cyclosporine, tacrolimus, sirolimus, everolimus, pimecrolimus, ABT-578, AP23573, CCI-779, interferons (IFN-β or IFN-γ), TNF binding proteins (infliximab, etanercept, or adalimumab), azathioprine, cyclosporine, corticosteroids, mycophenolic acid, fingolimod, myriocin, glucocorticoids, monoclonal antibodies, cyclophosphamide, mycophenolate mofetil, gusperimus, mizoribine, doxorubicin, adriamycin, azathiopurine, busulfan, deoxyspergualin, fludarabine, 5-fluorouracil, leflunomide (LEF); methotrexate, prednisolone, methylprednisolone, basiliximab, daclizumab, and/or muromonab. It is specifically contemplated that one or more of these agents may be excluded in some embodiments.

It is specifically contemplated that any of the active ingredients or immunosuppressant therapies or combinations thereof described herein may be excluded from the methods either alone or in a combination therapy.

IV. Sample Preparation

In certain aspects, methods involve obtaining a sample from a subject. The methods of obtaining provided herein may include methods of blood withdrawal or tissue biopsy, such as fine needle aspiration, core needle biopsy, vacuum assisted biopsy, incisional biopsy, excisional biopsy, punch biopsy, shave biopsy or skin biopsy. Alternatively, the sample may be obtained from any other source including but not limited to blood, sweat, hair follicle, buccal tissue, tears, menses, feces, or saliva. In certain aspects the sample is obtained from the serum of a patient. In certain aspects of the current methods, any medical professional such as a doctor, nurse or medical technician may obtain a biological sample for testing. Yet further, the biological sample can be obtained without the assistance of a medical professional.

Techniques for isolating autoantibodies from a blood/serum sample are well known in the art. The IgG purification may be performed using Melon Gel Kit (cat. N. 45206) according to the manufacturer instructions (Thermo Scientific, Pierce, Rockford, USA). IgG containing effluents can be saved and frozen at −20° C. before determining the affinity of the autoantibodies.

A sample may include but is not limited to blood, tissue, cells, or biological extracts of cells or cells derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen. In certain embodiments the samples are obtained by biopsy, swabbing, scraping, phlebotomy, or any other methods known in the art. In some cases, the sample may be obtained, stored, or transported using components of a kit of the present methods. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

In some embodiments of the present methods, the biological sample may be obtained from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist surgeon or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

V. Protein Assays

A variety of techniques can be employed to measure expression levels of polypeptides and proteins in a biological sample. Examples of such formats include, but are not limited to, enzyme immunoassay (EIA), radioimmunoassay (RIA), Western blot analysis, indirect immunofluorescence, immunodiffusion, immunoblotting, laser beads, antigen arrays, and enzyme linked immunoabsorbent assay (ELISA). A skilled artisan can readily adapt known protein/antibody detection methods for use in detecting GPIHBP1 autoantibodies.

In one embodiment, GPIHBP1 polypeptides, antibodies, or antibody fragments or derivatives, can be used in methods such as Western blots or immunofluorescence techniques to detect autoantibody expression. In some embodiments, either the antibodies or proteins (i.e. GPIHBP1 polypeptides) are immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody, autoantibody, or antigen, and will be able to adapt such support for use with the present disclosure. The support can then be washed with suitable buffers followed by treatment with the detectably labeled antibody, such as a labeled secondary antibody. The solid phase support can then be washed with the buffer a second time to remove unbound antibody. The amount of bound label on the solid support can then be detected by conventional means.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art. A two-site, monoclonal-based immunoassay utilizing antibodies reactive to two non-interfering epitopes or a competitive binding assay may be employed. In some embodiments, the immunoassay detects binding of LPL to GPIHBP1 in the presence of autoantibodies isolated from a patient sample.

Numerous labels are available and commonly known in the art. Antibodies or polypeptides can be labeled using the techniques known in the art. Radioisotope labels include, for example, $^{36}$S, $^{14}$C, $^{125}$I, $^{3}$H, and $^{131}$I. Fluorescent labels include, for example, labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques known in the art. Fluorescence can be quantified using a fluorimeter. Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzymology (Ed. J. Langone & H. Van Vunakis), Academic press, New York, 73: 147-166 (1981).

In some embodiments, a detection label is indirectly conjugated with an antibody or polypeptide, such as a GPIHBP1 polypeptide. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). In some embodiments, the antibody need not be labeled, and the presence thereof can be detected using a labeled antibody, which binds to the antibody.

VI. Pharmaceutical Compositions

In certain aspects, the compositions or agents for use in the methods, such as immunosuppressive agents or GPIHBP1 activators, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight can be administered.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VII. Kits

Certain aspects of the present disclosure also concern kits containing compositions of the disclosure or compositions to implement methods of the disclosure. In some embodiments, kits can be used to evaluate one or more nucleic acid and/or polypeptide molecules, such as autoantibodies, from a sample from a subject. In certain embodiments, a kit contains a GPIHBP1 polypeptide. In some embodiments, the polypeptide is a recombinant polypeptide. In some embodiments, the recombinant GPIHBP1 comprises an amino acid sequence with at least 80%, 85%, 90%, 91%, 92%, 93%, 94%, 95%, 96%, 97%, 98%, 99%, or 100% identity to SEQ ID NO:4 (or any range derivable therein). In some embodiments, the recombinant GPIHBP1 is produced in insect cells. In some embodiments, the recombinant GPIHBP1 is produced in mammalian cells. In some embodiments, the GPIHBP1 is purified. In some embodiments, the GPIHBP1 comprises human GPIHBP1. In some embodiments, the GPIHBP1 comprises a C-terminal portion that is non-human. In some embodiments, the non-human c-terminal portion comprises GPIHBP1 polypeptides from mouse GPIHBP1.

In some embodiments, the kit further comprises labeled anti-human IgG.

In some embodiments, the kit further comprises a LPL polypeptide. In some embodiments, the LPL polypeptide comprises a polypeptide from human LPL or a polypeptide that is at least 80%, 85%, 90%, 91%, 92%, 93%, 94%, 95%, 96%, 97%, 98%, 99%, or 100% identical to a human LPL polypeptide (or any range derivable therein).

A representative polypeptide of human LPL is:

(SEQ ID NO: 5)
MESKALLVLTLAVWLQSLTASRGGVAAADQRRDFIDIESKFALRTPEDTAE

DTCHLIPGVAESVATCHFNHSSKTFMVIHGWTVTGMYESWVPKLVAALYKR

EPDSNVIVVDWLSRAQEHYPVSAGYTKLVGQDVARFINWMEEEFNYPLDNV

HLLGYSLGAHAAGIAGSLTNKKVNRITGLDPAGPNFEYAEAPSRLSPDDAD

FVDVLHTFTRGSPGRSIGIQKPVGHVDIYPNGGTFQPGCNIGEAIRVIAER

GLGDVDQLVKCSHERSIHLFIDSLLNEENPSKAYRCSSKEAFEKGLCLSCR

KNRCNNLGYEINKVRAKRSSKMYLKTRSQMPYKVFHYQVKIHFSGTESETH

TNQAFEISLYGTVAESENIPFTLPEVSTNKTYSFLIYTEVDIGELLMLKLK

WKSDSYFSWSDWWSSPGFAIQKIRVKAGETQKKVIFCSREKVSHLQKGKAP

AVFVKCHDKSLNKKSG.

In some embodiments, the LPL polypeptide comprises a polypeptide tag. In some embodiments, the polypeptide tag is a V5 polypeptide tag. Other polypeptide tags are known in the art and include, for example, poly(His) tag, glutathione-S-transferase tag, chitin binding protein tag, maltose binding protein tag, thioredoxin tag, FLAG-gay, Myc tag, or HA tag.

In some embodiments, the kit further comprises a antibody that specifically binds to a LPL polypeptide or a polypeptide tag on the LPL polypeptide. In some embodiments, the antibody further comprises a detectable label.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more (or any range derivable therein).

Kits for using probes, polypeptide detecting agents, and/or activators of the disclosure for prognostic or diagnostic applications are included.

In certain aspects, negative and/or positive control agents are included in some kit embodiments.

It is contemplated that any method or composition described herein can be implemented with respect to any other method or composition described herein and that different embodiments may be combined.

Any embodiment of the disclosure relating to a polypeptide or nucleic acid is contemplated also to cover embodiments whose sequences are at least 80, 81, 82, 83, 84, 85, 86, 87, 88, 89, 90, 91, 92, 93, 94, 95, 96, 97, 98, 99% identical to the polypeptide or nucleic acid.

The kit can further comprise reagents for labeling probes, nucleic acids, polypeptides, antibodies, and/or detecting agents. The kit may also include labeling reagents, including at least one of amine-modified nucleotide, poly(A) polymerase, and poly(A) polymerase buffer. Labeling reagents can include an amine-reactive dye.

VIII. Examples

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. In the examples and throughout the disclosure, Protein-G variants are polypeptides comprising a Fab-binding region.

Example 1—ELISA for Detection of GPIHBP1 Autoantibodies

Human GPIHBP1 was cloned into a UPAR expression vector for Drosophila (Drosophila melanogaster). In some embodiments, the GPIHBP1 is modified to contain carboxyl terminal sequences from mouse GPIHPB1 so that detection or capture of the protein can be achieved with a monoclonal antibody against the carboxyl terminal region of GPIHBP1.

The sequence of the human GPIHBP1 with a N-terminus R24 epitope tag and a C-terminus 11A12 epitope tag is as follows:

```
DNA Sequence:
                                            (SEQ ID NO: 3)
  1   CGCCAGTGTT ACAGCTGCAA GGGGAACAGC ACCCATGGAT GCTCCTCTGA

61   AGAGACTTTC CTCATTGACT GCCGAGGCCC CATGAATCAA TGTCTGGTAG

111   CCACCGGCAC TCACGAACCG AAAAACCAAA GCTATATGGT AAGAGGCTGT

161   GCAACCGCCT CAATGTGCCA ACATGCCCAC CTGGGTGACG CCTTCAGCAT

211   GAACCACATT GATGTCTCCT GCTGTACTAA AAGTGGCTGT AACCACCCAG

261   ACCTGGATGT CCAGTACCGC AGTGGGCTCG AGgacgacga cgataagCAG

311   ACACAGCAGG AGGAAGAGGA AGAGGACGAG GACCACGGGC CAGATGACTA

361   CGACGAGGAA GATGAGGATG AGgtgGAAGA GGAGGAGACC AACAGGCTCC

411   CTGGTGGCAG GAGCAGAGTG CTGCTGCGGT GCTACACCTG CAAGTCCCTG

461   CCCAGGGACG AGCGCTGCAA CCTGACGCAG AACTGCTCAC ATGGCCAGAC

511   CTGCACAACC CTCATTGCCC ACGGGAACAC CGAGTCAGGC CTCCTGACCA

561   CCCACTCCAC GTGGTGCACA GACAGCTGCC AGCCCATCAC CAAGACGGTG
```

```
-continued
611    GAGGGGACCC AGGTGACCAT GACCTGCTGC CAGTCCAGCC TGTGCAATAT

661    TCCACCCTGG CAGAACCCCC AAGTCCAGAA CCCTCTGGGT GGCCGGGCAG

711    ACAGCCCCCT GGAAAGTGGG ACTAGACATC CTCAGGGTGG CAAGTTTAGC

761    CACCCCCAGG TTGTCAAGGC TGCTCATCCT CAGAGCGATG GGGCTAACTT

811    GCCTAAGAGT GGCAAGGCTA ACCAGCCCCA GTGA.
```

Amino Acid Sequence:
(SEQ ID NO: 4)
RQCYSCKGNSTHGCSSEETFLIDCRGPMNQCLVATGTHEPKNQSYMVRGCATASMCQHAHL GDAFSMNHIDVSCCTKSGCNHPDLDVQYRSGLEddddkQTQQEEEEEDEDHGPDDYDEEDED

EVEEEETNRLPGGRSRVLLRCYTCKSLPRDERCNLTQNCSHGQTCTTLIAHGNTESGLLTTHS

TWCTDSCQPITKTVEGTQVTMTCCQSSLCN*IPPWQNPQVQNPLGGRADSPLESGTRHPQGGKF*

*SHPQVVKAAHPQSDGANLPKSGKANQPQ*.

In the DNA and protein sequences above, the suPAR Domain III/R24 epitope tag is underlined and located at DNA position 1-286. The Enterokinase cleavage site is in lowercase and located at DNA position: 293-307. The hGPIHBP1 sequence is double underline and located at DNA position 308-655 and amino acid position Q21-G151. A silent mutation is in lowercase-double underline and located at DNA position 383-385. The mGPIHBP1 C-terminus/11A12 epitope tag is in italics and located at DNA position 656-844.

The advantage of having a uPAR tag in the expression vector (underlined region at DNA position 1-286 above), is that it allows the purification of human GPIHBP1 from the culture medium of insect cells on an antibody R24 column.

For the assay, medium from the host cells (comprising the recombinantly produced GPIHBP1) was used, and the GPIHBP1 was captured onto the wells of a 96-well plate with a monoclonal antibody (i.e. antibody R24), but one could also perform the assay by immunopurifying the UPAR-GPIHBP1 fusion protein on an immunoaffinity column, and then using the purified fusion protein to coat plates.

The UPAR tag can easily be cleaved and then the GPIHBP1 can be purified and used for coating the plates. Furthermore, one could also perform the assay by transfecting other host cells, such as mammalian cells, with an expression vector for a soluble form of human GPIHBP1, and then use a monoclonal antibody to capture the GPIHBP1.

Once the GPIHBP1 is immobilized on the plate, diluted human plasma is added. The plate is then washed, and anti-human IgG labeled with HRP is used to detect the presence of autoantibodies in the plasma sample.

In some embodiments, the assay further comprises the steps of testing for the inhibition of GPIHBP1-LPL binding by autoantibodies present in the human plasma. For this purpose, the GPIHBP1 is captured onto 96 well plates. The capture of the GPIHBP1 can be done as described above by coating the plate with the R24 antibody and adding the medium from the insect cells to capture the GPIHBP1. The plasma sample is then added. Next, a V5-tagged human LPL is added. The binding of human LPL to the immobilized GPIHBP1 is then accessed with a V5 antibody, and the amount of LPL bound to the immobilized human GPIHBP1 in the presence of the plasma sample versus the absence of the plasma sample is measured with an HRP-labeled V5 antibody. This assay is able to detect the ability of GPIHBP1 autoantibodies in a plasma to block the ability of the immobilized GPIHBP1 to bind LPL.

Example 2—Autoantibodies Against GPIHBP1 as a Cause of Hypertriglyceridemia

Glycosylphosphatidylinositol-anchored high-density lipoprotein binding protein 1 (GPIHBP1), a protein of capillary endothelial cells, binds lipoprotein lipase (LPL) and shuttles it to its site of action in the capillary lumen. A deficiency of GPIHBP1 prevents LPL from reaching the capillary lumen. Patients with GPIHBP1 deficiency have low levels of LPL in the plasma, impaired intravascular triglyceride hydrolysis, and severe hypertriglyceridemia (chylomicronemia). While characterizing a monoclonal antibody-based immunoassay for GPIHBP1, the inventors encountered two plasma samples, both from patients with chylomicronemia, that contained an interfering substance, making it impossible to measure GPIHBP1. That finding raised the possibility that those samples might contain GPIHBP1 autoantibodies.

A. Summary

Using a combination of immunoassays, western blots, and immunocytochemistry studies, the inventors tested the two plasma samples (as well as samples from other patients with chylomicronemia) for GPIHBP1 autoantibodies. The inventors also tested the ability of GPIHBP1 autoantibodies to block LPL binding to GPIHBP1.

GPIHBP1 autoantibodies were identified in six patients with chylomicronemia. These autoantibodies blocked LPL binding to GPIHBP1. Like patients with GPIHBP1 deficiency, those with GPIHBP1 autoantibodies had low levels of LPL in the plasma. Three of the six patients had systemic lupus erythematosus (SLE). One patient with SLE and GPIHBP1 autoantibodies delivered a baby whose plasma contained maternal GPIHBP1 autoantibodies; the infant had severe but transient chylomicronemia. Two chylomicronemia patients with GPIHBP1 autoantibodies responded to treatment with immunosuppressive agents.

GPIHBP1 autoantibodies block the ability of GPIHBP1 to bind and transport LPL, thereby interfering with LPL-mediated processing of triglyceride-rich lipoproteins and causing severe hypertriglyceridemia.

B. Introduction

Glycosylphosphatidylinositol-anchored high-density lipoprotein binding protein 1 (GPIHBP1), a protein in the lymphocyte antigen 6 (Ly6) superfamily that is expressed on the surface of capillary endothelial cells, binds lipoprotein lipase (LPL) in the interstitial spaces (where LPL is secreted by myocytes and adipocytes) and shuttles it to its site of action in the capillary lumen. In the setting of GPIHBP1 deficiency, LPL is mislocalized in the interstitial spaces and never reaches the capillary lumen, preventing the lipolytic processing of triglyceride-rich lipoproteins and causing severe hypertriglyceridemia (chylomicronemia). Many GPIHBP1 missense mutations causing chylomicronemia have been identified. All of these mutations disrupt the folding of GPIHBP1's Ly6 domain (the domain that binds LPL with high affinity) and block the ability of GPIHBP1 to bind LPL and transport it to the capillary lumen. A "signature" of GPIHBP1 deficiency in humans is low levels of LPL in the pre- and post-heparin plasma (reflecting a virtual absence of LPL inside capillaries). The inventors used monoclonal antibodies against human GPIHBP1 to create an enzyme-linked immunosorbent assay (ELISA) that can detect GPIHBP1 in human plasma.

The inventors encountered two plasma samples, both from patients with chylomicronemia, that contained an interfering substance, rendering it impossible to measure GPIHBP1 in those samples—or even to detect recombinant GPIHBP1 that had been spiked into those samples. The inventors hypothesized that the ELISA interference might be caused by GPIHBP1 autoantibodies. It was further hypothesized that these autoantibodies would abolish binding of LPL to GPIHBP1 and thereby cause chylomicronemia.

In this example, the inventors report the discovery of six patients with chylomicronemia who had high-titer specific GPIHBP1 autoantibodies, and the inventors show that these antibodies block the binding of LPL to GPIHBP1.

C. Methods

1. Study Patients

The initial study cohort, selected to assist in the development of the ELISA for GPIHBP1, included 23 patients known to have mutations in GPIHBP1 or LPL, 8 hypertriglyceridemic patients without mutations in GPIHBP1 or LPL, and 9 controls. After identification of two patients with GPIHBP1 autoantibodies (one with systemic lupus erythematosus [SLE], both with hypertriglyceridemia) in this initial cohort of 40 patients, the inventors then screened another 162 patients, seeking additional cases with such autoantibodies. These included 40 patients with SLE from the UCLA rheumatology clinic (half on immunosuppressive therapy), and 122 patients from lipid clinics (all with hypertriglyceridemia of unknown etiology).

All plasma samples from study patients (202 total) were either archived specimens obtained under institutional approval or samples sent from other investigators to the last author without identifiers and were therefore deemed by ULCA's Office of Human Use Protection to be exempt from institutional review board approval. Patient numbers throughout this report are the sample numbers recorded for specimen identification by the laboratory of the last author.

2. Enzyme-Linked Immunosorbent Assays (ELISAs)

A monoclonal antibody-based sandwich ELISA similar to those used to measure LPL and apolipoprotein B levels was developed to measure GPIHBP1 levels on plasma samples from study patients. 96-well ELISA plates were coated with the GPIHBP1-specific monoclonal antibody RF4. After adding plasma samples or standards, bound GPIHBP1 was detected with horseradish peroxidase (HRP)-labeled GPIHBP1-specific monoclonal antibody RE3.

To detect GPIHBP1 autoantibodies in plasma, 96-well plates were coated with human GPIHBP1 or GPIHBP1 containing an amino-terminal urokinase-type plasminogen activator receptor (uPAR) tag. After blocking with bovine serum albumin (BSA), plasma samples were added. After washing the plates, antibody binding to GPIHBP1 was detected with HRP-labeled goat anti-human Ig(G+M). The amount of GPIHBP1 autoantibodies (in arbitrary units) was judged by comparing ELISA signals to those in a parallel ELISA in which plates were coated with known amounts of human IgG. ELISAs were also used to test for autoantibodies against three other Ly6 proteins (CD177, C4.4A, and CD59).

To test the ability of GPIHBP1 autoantibodies to block LPL binding to GPIHBP1, 96-well plates coated with GPIHBP1 were incubated with dilutions of plasma samples overnight at 4° C. Plates were then incubated for 1 h at 4° C. with V5-tagged human LPL (200 ng/well). After washing, an HRP-V5 antibody was added to quantify bound LPL. In parallel, an HRP-labeled goat anti-human Ig(G+M) was added to document autoantibody binding to GPIHBP1. The presence of GPIHBP1 on the plates was verified with the HRP-labeled monoclonal antibody 11A12. As a control, the inventors tested the ability of the monoclonal antibody RE3 to block binding of LPL to GPIHBP1. Details regarding ELISAs are in other methods of this example.

3. Western Blot Assay of LPL-GPIHBP1 Binding

Cells expressing S-protein-tagged GPIHBP1 were incubated with V5-tagged human LPL. After washing and lysis, cell extracts were size-fractionated by SDS-PAGE, and the amount of LPL bound to cells was determined by western blot with a V5 antibody. To determine if GPIHBP1 autoantibodies blocked binding of LPL to GPIHBP1, the same assay was performed except that transfected cells were preincubated with plasma samples containing GPIHBP1 autoantibodies.

4. Immunocytochemistry

To visualize binding of GPIHBP1 autoantibodies, Chinese hamster ovary (CHO) cells expressing S-protein-tagged GPIHBP1 were incubated for 2 h at 4° C. with human plasma samples. After washing, cells were incubated with Alexa Fluor 488-conjugated goat anti-human Ig(G+M) for 1 h at 4° C. and then fixed with paraformaldehyde. GPIHBP1 expression was assessed with the monoclonal antibody RG3 or with an antibody against the S-protein tag.

To test the ability of the GPIHBP1 autoantibodies to block LPL binding, S-protein-tagged GPIHBP1-transfected cells were incubated for 1 h at 4° C. with human plasma samples. After washing, the cells were incubated for 1 h at 4° C. with V5-tagged human LPL. After washing the cells and fixation with methanol, cells were stained with an Alexa Fluor 488-conjugated goat anti-human Ig(G+M); a rabbit antibody against the S-protein tag followed by an Alexa Fluor 647-conjugated donkey anti-rabbit IgG; and an Alexa Fluor 555-conjugated mouse anti-V5 antibody 5. V5-Tagged Human LPL A stable CHO cell line expressing V5-tagged human LPL was adapted for growth in 95% serum-free/protein-free medium (ProCHO-AT, Lonza). Conditioned medium was concentrated 10-fold with Amicon Ultra 30 k MWCO filters (Millipore). The amount of LPL in conditioned medium was determined by western blotting against an LPL standard with an anti-V5 antibody (ThermoFisher Scientific).

6. A Sandwich ELISA to Measure LPL and GPIHBP1 Levels in Human Plasma

LPL levels were determined with a sandwich immunoassay at Immuno-Biological Laboratories, Fukojioka, Japan, and a GPIHBP1 sandwich ELISA was recently developed. For the GPIHBP1 ELISA, 96-well plates were coated with mAb RF4 (against GPIHBP1's acidic domain; 1 µg/well), and blocked in PBS containing 1% BSA and 0.05% NaN$_3$ before incubating with serial dilutions of the plasma samples or rhGPIHBP1 standards overnight at 4° C. After washing, the amount of captured GPIHBP1 was measured by incubating for 30 min at 4° C. with HRP-labeled mAb RE3 Fab' (against GPIHBP1's Ly6 domain; 0.5 µg/well). After washing, the plate was incubated with TMB substrate (Kem-en-Tec) for 30 min at room temperature. The reaction was stopped with 2 M sulfuric acid, and the optical density (OD) was read at 450 nm.

7. ELISAs to Detect GPIHBP1 Autoantibodies in Human Plasma

ELISA plates were coated with mAb R24 (0.5 µg/well) overnight at 4° C. Plates were washed and then blocked for 4 h at room temperature in Starting block buffer (Pierce). R24-tagged rhGPIHBP1 from the conditioned medium of stably transfected *Drosophila* S2 cells was added (0.5 µg/well) and incubated for 2 h at 4° C. After washing, plates were incubated in the presence of plasma samples (triplicates, 1:500 in blocking buffer) overnight at 4° C. After washing, plates were incubated for 30 min at room temperature with an HRP-labeled goat anti-human Ig(G+M) (Jackson ImmunoResearch, 1:50,000 in blocking buffer), and the GPIHBP1 autoantibody titer for each sample was determined against a human IgG standard curve. After washing plates extensively, 50 µl of ultra TMB ELISA substrate (Pierce) was added per well. The plate was incubated at room temperature for 5 min before stopping the reaction with 50 µl of 2 M sulfuric acid. The OD was immediately read at 450 nm on a Spectra Max 190 plate reader (Molecular Devices).

8. A Second ELISA to Detect GPIHBP1 Autoantibodies in Human Plasma

ELISA plates were directly coated (0.5 µg/well) with purified rhGPIHBP1, rhCD177, rhC4.4A, or rhCD59 overnight at 4° C. Plates were washed and then blocked for 4 h at room temperature in Starting block buffer (Pierce). After washing, plates were incubated in the presence of plasma samples (triplicates; 1:500 in blocking buffer for plasma 38, 101, 103, 111, 157, and 164 (1:12,500 for plasma 102) overnight at 4° C. After washing, the plate was incubated for 30 min at room temperature with an HRP-labeled goat anti-human Ig(G+M) (Jackson ImmunoResearch, 1:50,000 in blocking buffer). The GPIHBP1 autoantibody titer for each sample was judged against a human IgG standard (in which different amounts of human IgG were coated directly on the plate). In this way, the inventors obtained a measurement of titers of GPIHBP1 in arbitrary units. Plates were washed extensively, and 50 µl of ultra TMB ELISA substrate (Pierce) was added per well. The plate was incubated at room temperature for 5 min before stopping the reaction with 50 µl of 2 M sulfuric acid; the OD was read at 450 nm.

9. An ELISA to Assess the Ability of the GPIHBP1 Autoantibodies to Block LPL Binding Briefly, ELISA plates were coated with mAb R24 (0.5 µg/well) and blocked in Starting block buffer (Pierce). Next, rhGPIHBP1 was added (0.5 µg/well) in the presence or absence of serial 1:2 dilutions of plasma samples (or dilutions of mAb RE3) and incubated overnight at 4° C. The next day, the plate was incubated for 1 h at 4° C. with V5-tagged human LPL (200 ng/well). After washing, LPL bound to GPIHBP1 was detected by incubating for 1 h at 4° C. with an HRP-V5 antibody (ThermoFisher Scientific, 1:5,000). Autoantibodies bound to GPIHBP1 were detected by incubating duplicate wells with an HRP-labeled goat anti-human Ig(G+M) (Jackson ImmunoResearch, 1:50,000). In a control experiment, the ability of mAb RE3 to block the binding of LPL to GPIHBP1 was tested. After washing, each well was incubated with TMB substrate (Pierce). After 5 min, the reaction was stopped with 2 M sulfuric acid; the OD was read at 450 nm.

10. A Cell-Based LPL-GPIHBP1 Binding Assay

Expression vectors for S-protein-tagged wild-type (wt) GPIHBP1, GPIHBP1-G175R, and GPIHBP1-W109S (or the empty vector) were transfected into CHO pgsA-745 cells or human umbilical vein endothelial cells (HUVEC). After 1 day, the cells were washed three times in PBS and incubated for 1 h at 4° C. with V5-tagged human LPL (900 ng/well). Then the cells were washed six times in PBS, and cell lysates were collected in RIPA buffer (Sigma) containing a protease inhibitor cocktail (Roche). Proteins were separated by SDS-PAGE, and western blots were performed under reducing conditions with a goat antibody against the S-protein tag (Abcam, 5 µg/ml), followed by an IRdye680-donkey anti-goat IgG (LI-COR, 1:2000) and an IRdye800-V5 antibody (1:500).

When testing the ability of GPIHBP1 autoantibodies to block LPL binding to GPIHBP1 on GPIHBP1-expressing CHO pgsA-745 cells, the cells were pre-incubated for 1 h at 4° C. with plasma sample 3 (negative for GPIHBP1 autoantibodies; 1:20 dilution in PBS), plasma sample 38 (positive for GPIHBP1 autoantibodies; 1:20 in PBS), or mAb RG3 (20 µg/ml) before adding the LPL.

11. Immunocytochemistry Studies to Test the Ability of GPIHBP1 Autoantibodies in Plasma 38 to Bind to GPIHBP1

CHO pgsA-745 cells were transfected with expression vectors for S-protein-tagged versions of wild-type human GPIHBP1 or human CD59. The next day, cells were washed three times with PBS. The cells were first blocked in 10% goat serum for 1 h at 4° C. and then incubated for 2 h at 4° C. with plasma 38 (diluted 1:20 in PBS). Cells were washed six times in 3% goat serum and incubated for 1 h at 4° C. with Alexa488-conjugated goat anti-human Ig(G+M) (Jackson ImmunoResearch, 2.5 µg/ml). After washing, cells were fixed in 3% PFA, and immunocytochemistry studies were performed on nonpermeabilized cells with a rabbit antibody against the S-protein tag (Abcam, 0.4 µg/ml, 1-h incubation at room temperature), an Alexa568-conjugated donkey anti-rabbit IgG (ThermoFisher Scientific, 2.5 µg/ml, 30-min incubation at room temperature), mAb RG3 (5 µg/ml, 1-h incubation at room temperature), and an Alexa647-conjugated donkey anti-mouse IgG (ThermoFisher Scientific, 2.5 µg/ml, 30-min incubation at room temperature). Coverslips were then mounted on slides with Prolong antifade plus DAPI (ThermoFisher Scientific).

In another experiment, the ability of the GPIHBP1 autoantibodies in plasma 38 was compared to the ability of mAb RF4 to bind to GPIHBP1 on GPIHBP1-transfected cells. Briefly, the cells were incubated for 2 h with plasma 38 (diluted 1:100 in PBS) at 4° C. Next, the cells were fixed in 3% PFA. After washing, the cells were blocked in 10% normal goat serum for 1 h at room temperature, and immunocytochemistry studies were performed on nonpermeabilized cells with an Alexa488-conjugated goat anti-human Ig(G+M) (Jackson ImmunoResearch, 2.5 µg/ml, 30-min incubation at room temperature), a rabbit antibody against the S-protein tag (Abcam, 0.4 µg/ml, 1-h incubation at room temperature), an Alexa568-conjugated donkey anti-rabbit IgG (ThermoFisher Scientific, 2.5 µg/ml, 30-min incubation at room temperature), mAb RF4 (5 µg/ml, 1-h incubation at room temperature), and an Alexa647-conjugated donkey anti-mouse IgG (ThermoFisher Scientific, 2.5 µg/ml, 30-min incubation at room temperature). Coverslips were then mounted on slides with Prolong antifade plus DAPI (ThermoFisher Scientific).

All images were recorded with an Axiovert 200M microscope and processed with the Zen 2010 software (Zeiss).

12. Immnunocytochemistry Studies to Test the Ability of the Autoantibodies to Block LPL Binding to GPIHBP1

Expression vectors for S-protein-tagged human wild-type (wt) GPIHBP1 or GPIHBP1-W109S were transfected into CHO pgsA-745 cells. After 24 h, the cells were washed three times in PBS. The transfected cells were then incubated for 1 h at 4° C. with the human plasma samples (20 AU of GPIHBP1 autoantibodies/ml in PBS). Cells were washed three times in PBS and incubated for 1 h at 4° C. with V5-tagged human LPL (200 ng/well). Cells were then washed six times in PBS and fixed in chilled 100% methanol. The immunocytochemistry studies were performed on nonpermeabilized cells with an Alexa488-conjugated goat anti-human Ig(G+M) (50 ng/ml, 30-min incubation at room temperature), a rabbit antibody against the S-protein tag (0.2 µg/ml, 1-h incubation at room temperature), an Alexa647-conjugated donkey anti-rabbit IgG (ThermoFisher Scientific, 2.5 µg/ml, 30-min incubation at room temperature), and an Alexa555-conjugated mouse anti-V5 antibody (1:50, overnight at 4° C.). Coverslips were then mounted on Prolong antifade plus DAPI. Images were recorded with an Axiovert 200M microscope and processed with the Zen 2010 software (Zeiss). Within each experiment, the exposure conditions for each construct and each plasma sample were identical. 13. Recombinant Human GPIHBP1

A secreted version of recombinant wild-type human GPIHBP1 (rhGPIHBP1) with an amino-terminal uPAR tag (detectable by mAb R24) and a carboxyl-terminal 11A12 epitope tag was expressed in *Drosophila* S2 cells. The culture medium was filter-concentrated 20-fold with Amicon Ultra 10 k MWCO filters (Millipore). The amount of GPIHBP1 in the conditioned medium was determined by western blotting with mAb 11A12 and a purified GPIHBP1 standard. In some cases, rhGPIHBP1 was purified on a mAb R24 immunoaffinity column. Recombinant human Ly6 proteins (C4.4A, CD177 and CD59) with a uPAR tag were expressed in *Drosophila* S2 cells as previously described. The *Drosophila* cell line expressing uPAR-tagged CD177 was provided by Dr. H. Gardsvoll (Finsen Laboratory, Denmark).

14. Detecting GPIHBP1 Autoantibodies with Western Blots

The medium from rhGPIHBP1-expressing *Drosophila* S2 cells was size-fractioned on 12% Bis-Tris SDS-polyacrylamide gels and then transferred to a nitrocellulose membrane. After blocking in Odyssey blocking buffer (LI-COR), membranes were incubated with plasma samples (diluted to 20 AU of GPIHBP1 autoantibody/ml in blocking buffer), and the binding of autoantibodies to GPIHBP1 was detected with an IRdye680-goat anti-human IgG (1:200). rhGPIHBP1 was also detected with an IRdye800-RF4 (1:500).

15. Releasing GPIHBP1 from Cells with Phosphatidylinositol-Specific Phospholipase C (PIPLC)

Expression vectors for S-protein-tagged wild-type (wt) GPIHBP1, GPIHBP1-G175R, and GPIHBP1-W109S were transfected into both CHO pgsA-745 cells and HUVECs. The next day, cells were washed three times in PBS and then incubated for 15 min with PIPLC (10 U/ml) at 37° C. The culture medium and cell lysates were collected, and proteins were separated by SDS-PAGE under reducing or nonreducing conditions. Western blots were performed on culture medium and cell lysates with a goat anti-S-protein antibody (5 µg/ml) followed by an IRdye800-donkey anti-goat IgG (1:800). Actin was used as a loading control.

D. Results

1. ELISA Interference and GPIHBP1 Autoantibodies

Using the sandwich ELISA, GPIHBP1 levels in normal control plasma samples were 239-1110 pg/ml, while they were quite low in two patients with a homozygous C89X GPIHBP1 mutation (patients 11 and 15; 3 and 6 pg/ml, respectively) and in a patient with a homozygous GPIHBP1 deletion (patient 3; 36 pg/ml) (Table 1).

TABLE 1

Biochemical Characteristics of Patients with GPIHBP1 Autoantibodies and Patients with a Genetic Deficiency in GPIHBP1.

| ID | TG (mg/dl) | GPIHBP1 autoAbs (AU/ml) | GPIHBP1 (pg/ml) | LPL ng/ml | Mutation |
|---|---|---|---|---|---|
| 3 | >25,000 | ND | 36 | 7.3 | GPIHBP1 null (homozygous) |
| 6 | 6,480 | ND | 31 | 13.1 | GPIHBP1-C68Y (homozygous) |
| 39 | 468 | ND | 11 | 18.5 | GPIHBP1-C89F/null (compound |
| 11 | 1,524 | ND | 3 | 70.6 | GPIHBP1-C89X (homozygous) |
| 15 | 4,665 | ND | 6 | 11.9 | GPIHBP1-C89X (homozygous) |
| 21 | 3,164 | ND | 7 | 7.9 | GPIHBP1-S107C (homozygous) |
| 27 | 842 | ND | 9 | 10 | GPIHBP1-S107C (homozygous) |
| 28 | 673 | ND | 9 | 7.3 | GPIHBP1-S107C (homozygous) |
| 35 | 329 | ND | 9 | 11.7 | GPIHBP1-R76C (homozygous) |
| 36 | 1,175 | ND | 7 | 11.2 | GPIHBP1-R76C (homozygous) |
| 40 | 843 | ND | 24 | 16 | GPIHBP1-R76C (homozygous) |
| 37 | 1,954 | ND | 735 | 0.2 | LPL-Y315X (homozygous) |
| 38 | 2,660 | 327 | 85 | 9.8 | |
| 101 | 1,696 | 70 | 29 | 4.6 | |
| 111 | 1,389 | 98 | 9 | 32.1 | |
| 157 | 549 | 134 | 156 | 16.9 | |
| 164 | 4,784 | 196 | NT | 10 | |

TABLE 1-continued

Biochemical Characteristics of Patients with GPIHBP1 Autoantibodies and Patients with a Genetic Deficiency in GPIHBP1.

| ID | TG (mg/dl) | GPIHBP1 autoAbs (AU/ml) | GPIHBP1 (pg/ml) | LPL ng/ml) | Mutation |
|---|---|---|---|---|---|
| 102 | 6,500 | 2,366 | 4 | 5.8 | |
| 103 | 9,090 | 81 | NT | NT | |

ND, not detected;
NT, not tested;
TG, triglyceride;
autoAbs, autoantibodies;
AU, arbitrary unit.

Shown in table 1 are plasma triglyceride levels, GPIHBP1 autoantibody levels, plasma GPIHBP1 levels, and pre-heparin LPL levels in plasma samples containing GPIHBP1 autoantibodies (38, 101, 102, 103, 111, 157, and 164). GPIHBP1- and LPL-deficient patients were included for reference. The pre-heparin LPL plasma levels in normal control subjects and GPIHBP1-deficient subjects were 80.5±20.5 ng/ml (n=9) and 11.5±3.7 (n=10), respectively. The pre-heparin LPL plasma levels in patients with GPIHBP1 autoantibodies ranged from 5.8 to 32.1 ng/ml. The plasma GPIHBP1 levels in normal control subjects ranged from 239 to 1110 pg/ml (n=9). In subjects who were homozygous for GPIHBP1 mutations, the GPIHBP1 levels ranged from 3 to 36 pg/ml (n=11).

To validate the ELISA, the inventors spiked recombinant GPIHBP1 into 40 plasma samples. In 38 samples, the recovery of spiked GPIHBP1 was 98.8±3.8%. However, in samples from two patients with chylomicronemia and low plasma GPIHBP1 levels (patients 38 and 101; GPIHBP1 levels of 85 and 29 pg/ml, respectively), the recovery of spiked GPIHBP1 was extremely low (6.8 and 4.4%, respectively) (FIG. 1), indicating assay interference. Plasma sample 101 was from a 53-year-old Japanese female with a 25-year history of systemic lupus erythematosus (SLE) and severe hypertriglyceridemia (500-5,000 mg/dl) (Table 1). Plasma sample 38 was from a 26-year-old man with severe hypertriglyceridemia (5,572 mg/dl) complicated by pancreatitis. No LPL mutations were identified in either patient.

Figure 10:
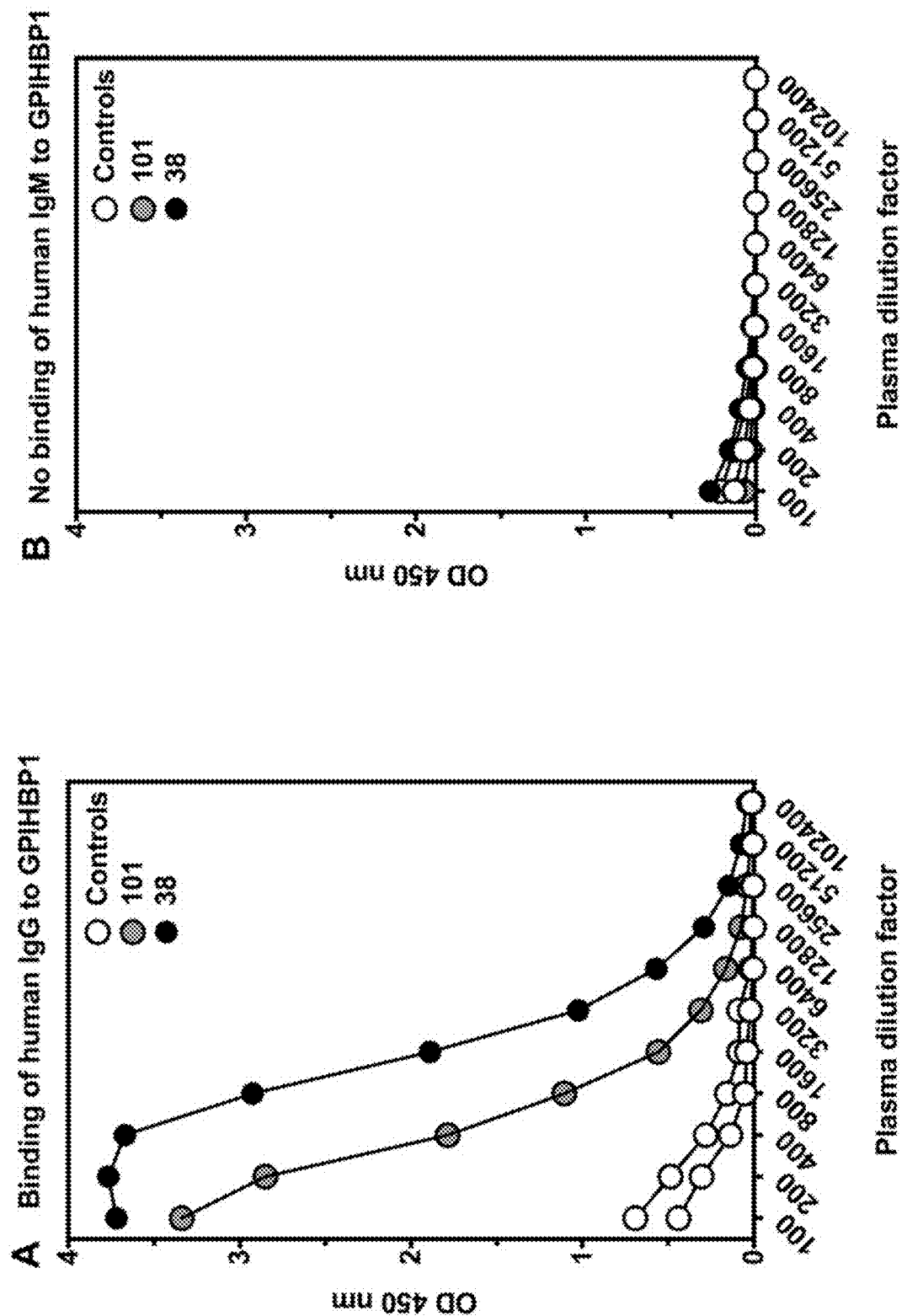
FIG. 10. GPIHBP1 Autoantibodies are IgGs, not IgMs. Panel (A) shows an ELISA, revealing that the GPIHBP1-binding immunoglobulins in plasma samples 38 and 101 are IgG. Panel (B) shows that the GPIHBP1 autoantibodies in plasma samples 38 and 101 are not IgM.

The inventors suspected that the ELISA interference in samples 38 and 101 was caused by GPIHBP1 autoantibodies. Indeed, GPIHBP1 autoantibodies were detectable by western blotting (FIG. 2A). ELISAs showed that the autoantibodies are IgG and not IgM (FIG. 10). The autoantibodies in sample 38 bound avidly to GPIHBP1-transfected CHO pgsA-745 cells but not to nontransfected cells or cells transfected with CD59 (another Ly6 protein) (FIG. 2B). A control plasma (sample 3) did not bind to GPIHBP1-transfected cells (FIG. 2B).

2. Additional Plasma Samples with GPIHBP1 Autoantibodies

The inventors used an ELISA to screen for GPIHBP1 autoantibodies in 130 plasma samples from patients with unexplained hypertriglyceridemia, several of whom had SLE or Sjögren's syndrome (FIG. 3(A)). The inventors also screened plasma samples from 40 SLE patients, half of whom were already on immunosuppressive therapy. None of the 40 SLE patients had severe hypertriglyceridemia (>750 mg/dl), and none had GPIHBP1 autoantibodies. Of the 130 patients with unexplained hypertriglyceridemia, 124 were negative for GPIHBP1 autoantibodies and 6 were positive (patients 38 and 101, plus four additional patients, namely 111, 157, 102, and 164).

All of the patients who were positive for GPIHBP1 antibodies had severe hypertriglyceridemia complicated by pancreatitis; clinical and laboratory details are provided in Tables 1 and 2. The hyperlipidemia in patient 157, a 26-year-old female with SLE, resolved with immunosuppressive drugs. When patient 164, a 9-year-old female with Sjögren's syndrome, was treated with immunosuppressive drugs, the plasma triglyceride levels normalized and GPIHBP1 autoantibodies were no longer detectable in the plasma. Patient 102, a 38-year-old female with SLE, delivered a baby girl; blood samples from the baby (patient 103) on the first day of life had maternal GPIHBP1 autoantibodies and triglyceride levels of 9,090 mg/dl. By one year of age, the plasma triglyceride levels normalized (72 mg/dl).

Figure 3:
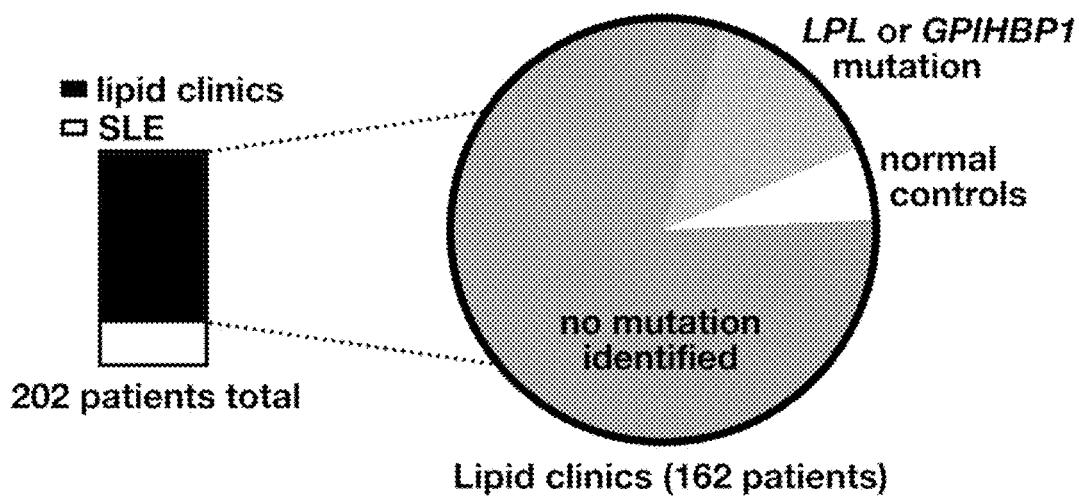
FIG. 3. Identification of Four Additional Plasma Samples with GPIHBP1 Autoantibodies. Panel (A) summarizes the plasma samples screened for GPIHBP1 autoantibodies. The studies were performed on a total of 202 de-identified archived plasma samples from lipid (black) or rheumatology (white) clinics. Forty SLE patients, half of them on immunosuppressive therapy, were included; 10 of those patients had plasma triglyceride levels between 350 and 750 mg/dl. The 162 lipid clinic patients included 130 male and female hypertriglyceridemic patients with no known genetic etiology (dark grey), 23 hypertriglyceridemic patients with a mutation in GPIHBP1 or LPL (medium grey), as well as 9 wild-type relatives of patients with GPIHBP1 mutations (normal controls; light grey). Panel (B) shows western blots demonstrating that the immunoglobulins in plasma samples 102, 157, 111, and 164 (20 AU GPIHBP1 autoantibody/ml) bind preferentially to nonreduced human GPIHBP1. The lower panels show the same blots incubated with the human GPIHBP1-specific monoclonal antibody RF4 (4 µg/ml). The monoclonal antibody RF4 binds to reduced (R) and nonreduced (NR) forms of GPIHBP1 and to GPIHBP1 multimers, and was used as a loading control. C, negative control (culture medium from S2 cells that do not express human GPIHBP1). Panel (C) shows results from ELISAs, revealing that the immunoglobulins in plasma samples 38, 101, 102, 111, 157, 103, and 164 bind to wells of an ELISA plate coated with purified human GPIHBP1 but not to wells coated with other human Ly6 proteins (CD177, C4.4A, CD59). Sample 102 was diluted 1:12,500, other samples were diluted 1:500. A control plasma sample did not bind to any of the Ly6 proteins. Panel (D) shows a western blot, using monoclonal antibody R24, of purified Ly6 proteins (CD177, C4.4A, GPIHBP1, CD59) that had been size-fractionated on an SDS-polyacrylamide gel. All four proteins had an amino-terminal uPAR tag that could be detected with monoclonal antibody R24. This western blot documents that similar amounts of all four Ly6 proteins were used to coat 96-well plates for the ELISA in Panel (C).
Figure 3:
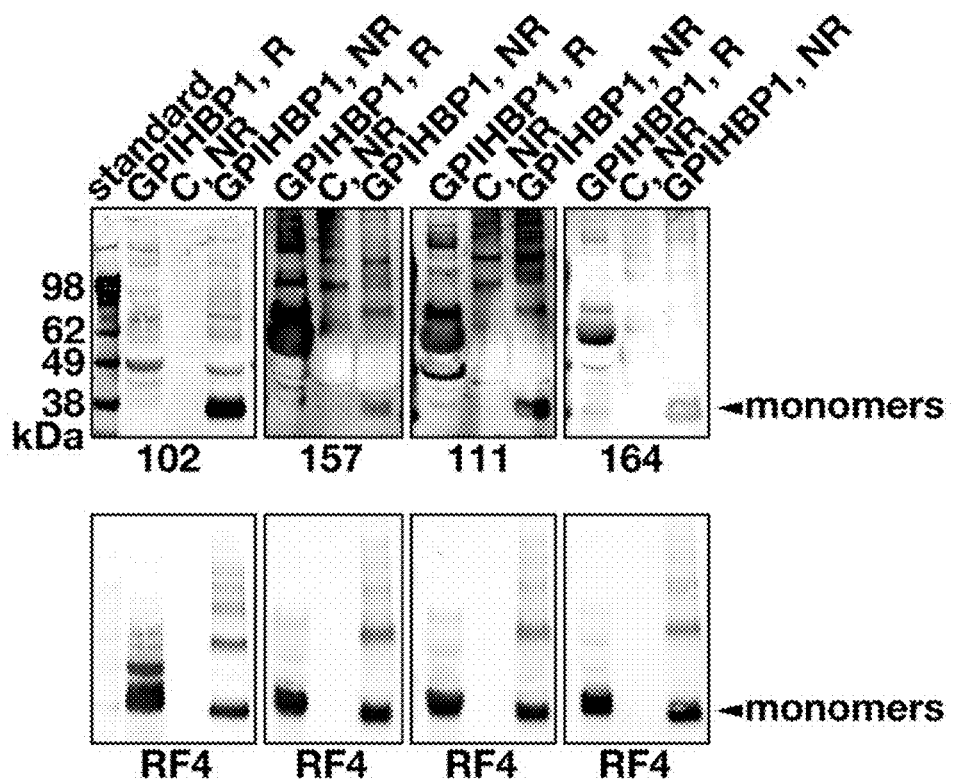
Figure 3:
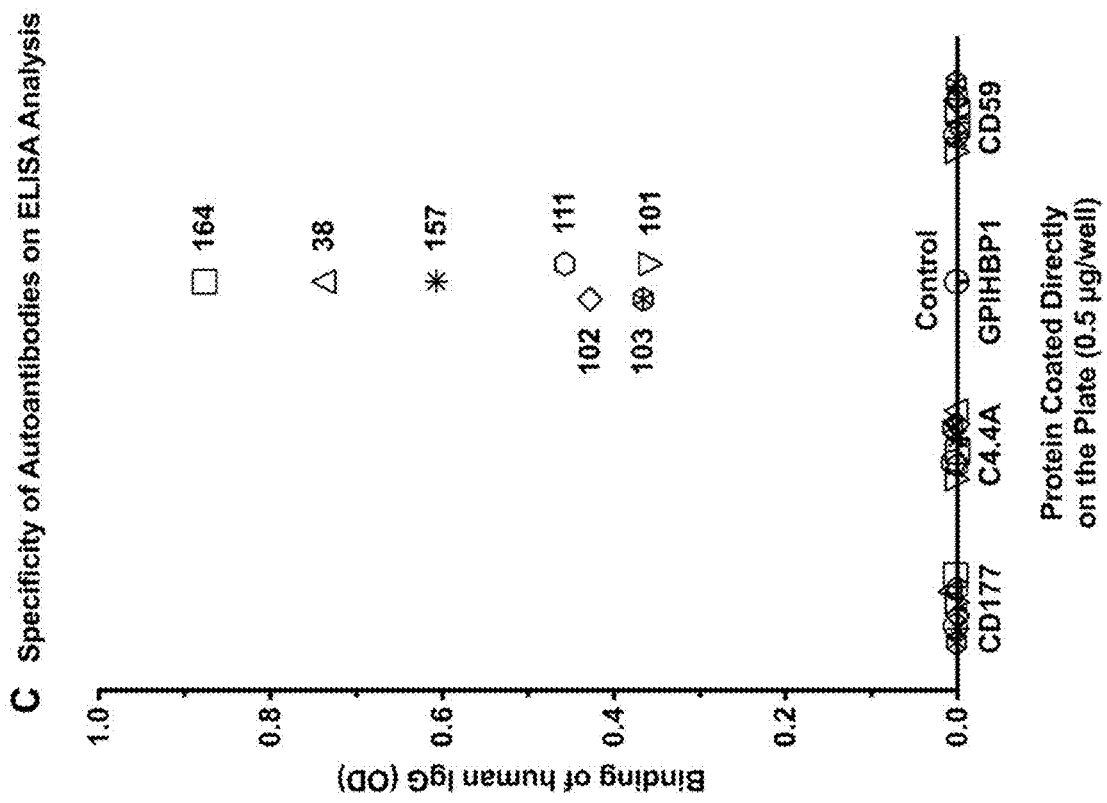

Western blots revealed GPIHBP1 autoantibodies in plasma samples 102, 111, 157, and 164 (FIG. 3(B)). In these cases, the autoantibodies bound poorly to GPIHBP1 treated with reducing agents, implying that the epitopes for the autoantibodies required the proper conformation of GPIHBP1's cysteine-rich Ly6 domain (the domain that mediates LPL binding). The GPIHBP1 autoantibody plasma samples (38, 101, 102, 111, 157, 103, and 164) were negative for autoantibodies against three other Ly6 proteins (CD177, C4.4A, and CD59) (FIGS. 3(C and D)).

3. GPIHBP1 Autoantibodies and Binding of LPL to GPIHBP1

For GPIHBP1 autoantibodies to cause hypertriglyceridemia, they would need to block LPL binding to GPIHBP1. To explore that possibility, the inventors tested the ability of one GPIHBP1 autoantibody plasma (38) and a control plasma (3) to block the binding of V5-tagged human LPL to GPIHBP1-expressing CHO cells. Only plasma 38 blocked LPL binding, as judged by western blots of cell extracts (FIG. 4A). The inventors also used immunocytochemistry studies to test the ability of the GPIHBP1 autoantibodies to block the binding of LPL to the surface of GPIHBP1-transfected cells. Autoantibodies in plasmas 102 and 111 blocked binding of LPL to GPIHBP1 on the cell surface (FIG. 4B). The immunoglobulins in plasma 3 bound weakly and nonspecifically to cells and did not block LPL binding (FIG. 4B).

The inventors used ELISAs to assess the ability of GPIHBP1 autoantibodies to block LPL binding to GPIHBP1 and simultaneously determined autoantibody titers (FIG. 5). Plasma samples 38, 101, 102, 111, 157, and 164 blocked LPL binding in a dose-dependent fashion (FIG. 5(A)). Plasma 102 had the highest titers of autoantibodies against GPIHBP1 (FIG. 5(B)) and was most potent in blocking LPL binding. The sample from the infant (103) also blocked LPL binding to GPIHBP1 (FIG. 5(A)) even though the titer of GPIHBP1 autoantibodies was <5% of those in the infant's mother (FIG. 5(B), Table 1).

4. Levels of LPL in Plasma Samples with GPIHBP1 Autoantibodies

The levels of LPL in the pre-heparin plasma of normal individuals are 50-77 ng/ml. The inventors measured pre-heparin LPL plasma levels in patients homozygous for missense or nonsense mutations in GPIHBP1 and found them to be low in most cases (ranging from 7.3 to 70.6 ng/ml) (Table 1). These findings are similar to those in earlier studies and are consistent with impaired transport of LPL to the capillary lumen. One would predict that plasma LPL levels in GPIHBP1 autoantibody patients would also be low if the GPIHBP1 autoantibodies truly caused the chylomicronemia (i.e., if the autoantibodies blocked LPL binding and transport). Indeed, the LPL levels in autoantibody plasma samples were low (ranging from 4.6 to 32.1 ng/ml) (Table 1), consistent with impaired delivery of LPL to the capillary lumen.

E. Supplementary Results

This section includes additional descriptions of patients with GPIHBP1 autoantibodies.

Figure 7:
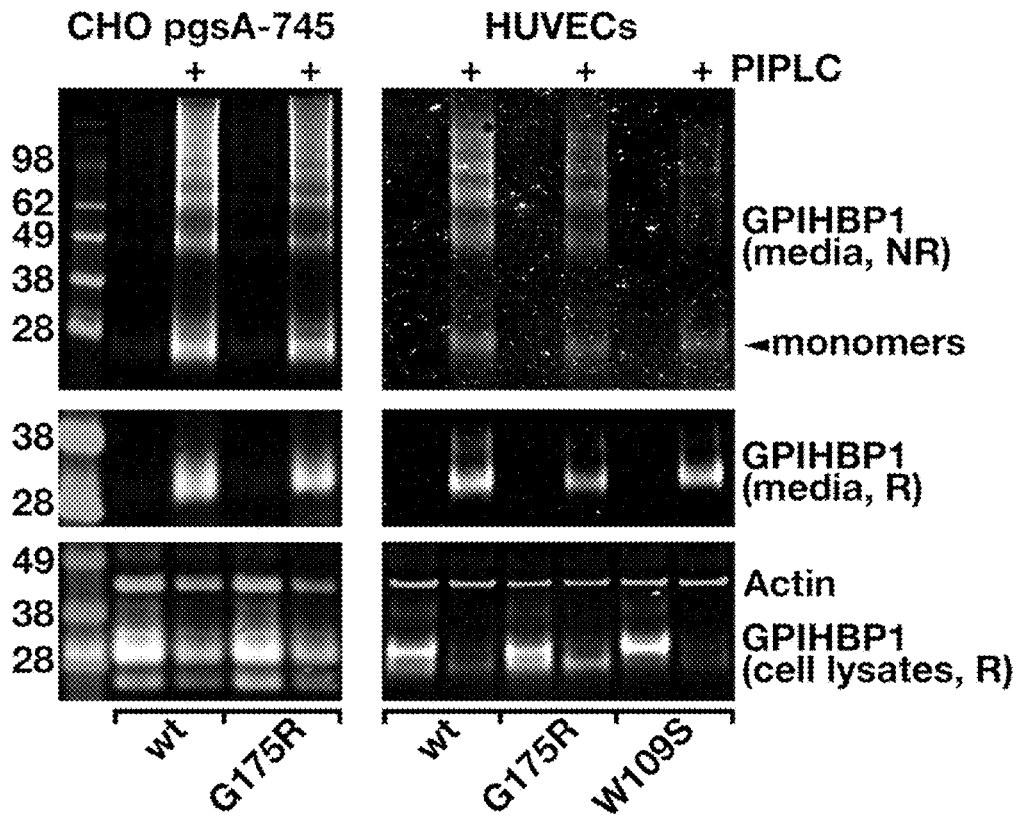
FIG. 7. GPIHBP1-G175R is a GPI-anchored protein and it binds LPL avidly. Panel (A) shows that GPIHBP1-G175R is GPI-anchored quite normally. Expression vectors for S-protein-tagged wild-type (wt) GPIHBP1, GPIHBP1-G175R, and GPIHBP1-W109S (a mutant that cannot bind LPL) were transfected in CHO pgsA-745 cells and HUVECs. GPIHBP1-G175R was released from the cell-surface with phosphatidylinositol-specific phospholipase C (PIPLC), which cleaves GPI anchors. The impact of the G175R mutation on the addition of the GPI anchor was minimal. Panel (B) shows that GPIHBP1-G175R did not have a reduced ability to bind LPL, when compared to GPIHBP1-wt. NR, nonreduced; R, reduced.
Figure 7:
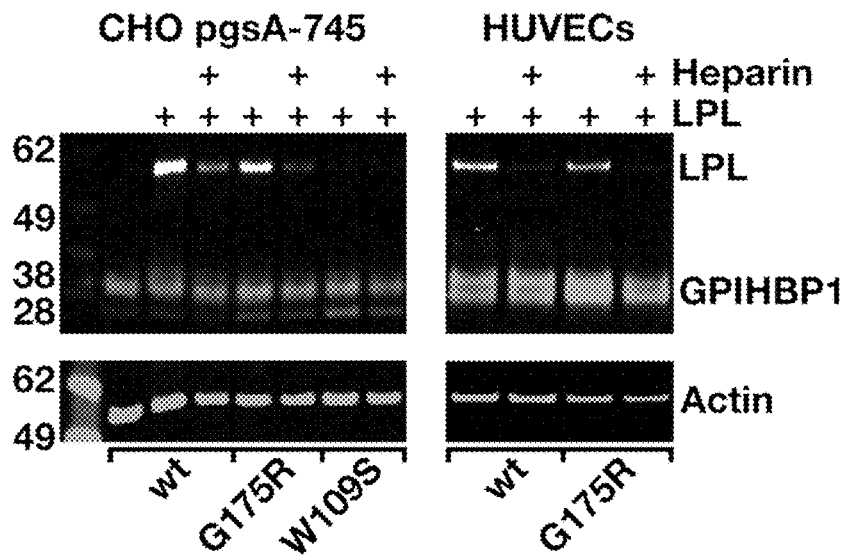

Patient 38, now deceased, was described previously. Briefly, this 26-year-old French male of Algerian origin with a history of abdominal pain since age 16, was referred for severe hypertriglyceridemia (2,301 mg/dl) and acute pancreatitis. Hypertriglyceridemia (885-5,752 mg/dl) and recurrent pancreatitis persisted despite a low-fat diet, fibrate therapy, and n–3 fatty acid supplements. The post-heparin LPL activity levels in plasma were extremely low. He had no disease-causing mutations in LPL, APOC2, APOA5, or LMF1. Ultimately, he developed insulin-dependent diabetes and exocrine pancreatic insufficiency with fat malabsorption. He died in Algeria at age 39 after multiple episodes of ketoacidosis and malnutrition in the context of psychiatric disorders. Patient 38 was homozygous for a G175R missense mutation in GPIHBP1. The G175R substitution was unique when it was reported but since has been observed many times in exome sequencing studies (rs145844329). This substitution introduces a positively charged amino acid into GPIHBP1's carboxyl-terminal hydrophobic domain. Initially, this substitution was assumed to prevent normal GPIHBP1 production by interfering with the addition of the GPI anchor. However, this is not the case, as illustrated by FIGS. 7(A and B). In both CHO cells and endothelial cells, GPIHBP1-G175R is expressed on the cell surface as a GPI-anchored protein and is released with phosphatidylinositol-specific phospholipase C (PIPLC) (FIG. 7(A)). GPIHBP1-G175R on the cell surface binds LPL avidly (FIG. 7(B)).

The mother and daughter of subject 38 were heterozygous for the G175R substitution and were normolipidemic. Both parents were born in the same region of Algeria but there was no history of consanguinity. The mother was diabetic and was taking steroids for rheumatoid arthritis. Patient 38 was never diagnosed with any autoimmune disease and tested negative for antinuclear antibodies.

Patient 101, a 53-year-old female from Japan with an unremarkable family history, had uneventful pregnancies at ages 29 and 31, but at age 34 she was diagnosed with hypertriglyceridemia, early rheumatoid arthritis (positive for anti-CCP antibody, 6 IU/ml; positive for RF, 63 IU/ml), and Sjögren's syndrome (strongly positive for anti-SS-A and anti-SS-B antibodies). At age 40, she had pancreatitis and was diagnosed with Hashimoto disease (anti-TPO antibody, >600 IU/ml, anti-thyroglobulin antibody, >4000 IU/ml; TSH, 10 mIU/L) and SLE (positive for anti-DNA and anti-cardiolipin antibodies). In the last 5 years, her plasma triglyceride levels have ranged from 723 to 4980 mg/dl. Screening for >30 LPL mutations was negative. She currently is treated with levothyroxine (50 m/day), prednisolone (10 mg/day), and salazosulfapyridine (1000 mg/day).

Patient 111, a 20-year-old female from France, presented at age 5 with pancreatitis and unexplained hypertriglyceridemia (6,062 mg/dl). She had 4 episodes of acute pancreatitis between the ages of 5 and 15. Her post-heparin LPL activity level was 3.9 mol/L/min (approximately 10% of normal values). She had no mutations in GPIHBP1, LPL, APOC2, APOA5, or LMF1. She was negative for antinuclear antibodies (ANA), anti-thyroid peroxidase antibodies (TPO), anti-neutrophil cytoplasmic antibodies (ANCA), anti-Sjögren's-syndrome-related antigen A (SSA) antibodies, and anti-Sjögren's syndrome type B (SSB) antibodies. Her hypertriglyceridemia (1500-6500 mg/dl) has been resistant to conventional drug therapies for hypertriglyceridemia (fenofibrate, high doses of n–3 fatty acids) and also resistant to dietary interventions. A trial of mycophenolate mofetil failed to lower the plasma triglyceride levels (Table 2).

TABLE 2

Follow-up Studies on Living Patients with Hypertriglyceridemia and GPIHBP1 Autoantibodies

| ID | ANA | Autoimmune disease diagnosis | Immunosuppressive treatment | Follow-up (mg/dl) | Follow-up autoAbs |
|---|---|---|---|---|---|
| 101 | +++ | Rheumatoid arthritis Sjögren's syndrome Hashimoto disease SLE | Prednisolone (10 mg/day) Salazosulfapyridine (1000 mg/day) | 1,137[a] | 54[a] |
| 111 | − | No autoimmune diagnosis | Mycophenolate mofetil | 2,573-4,085 | NSA[b] |
| 164 | +++ | Sjogren's syndrome | Mycophenolate mofetil (750 + 500 mg/day) Hydroxychloroquine (100 mg/day) | 37 | undetectable |
| 102 | +++ | SLE | Prednisone (5 mg/day) | NSA[c] | NSA[c] |

TABLE 2-continued

Follow-up Studies on Living Patients with Hypertriglyceridemia and GPIHBP1 Autoantibodies

| ID | ANA | Autoimmune disease diagnosis | Immunosuppressive treatment | Follow-up (mg/dl) | Follow-up autoAbs |
|---|---|---|---|---|---|
| 103 | ++ | Neonatal lupus (maternal GPIHBP1 autoantibodies causingchylomicronemia) GPIHBP1 G | None | 72 | NSA[c] |

SLE, systemic lupus erythematosus;
TG, triglyceride;
autoAbs, autoantibodies;
AU, arbitrary unit;
NSA, no sample available for testing.
[a]A follow-up plasma sample from patient 101 revealed persistence of both hypertriglyceridemia and GPIHBP1 antibodies. The plasma triglyceride level in the initial sample was 1,696 mg/dl, and the GPIHBP1 autoantibody titer was 70 AU/ml.
[b]Follow-up plasma samples from patient 111 during mycophenolate mofetil therapy were requested but not received.
[c]Patient 102 and her baby (patient 103) moved to Southeast Asia. The plasma triglyceride level in patient 103 at 1 year of age was 72 mg/dl.

Table 2 shows autoimmune disease diagnosis, antinuclear antibody (ANA) status, immunosuppressive drug treatment, follow-up plasma triglyceride levels after treatment, and GPIHBP1 autoantibody levels after treatment.

Her mother and sister are normotriglyceridemic. Her father, 46-years-old, was born in Vietnam and has Kimura disease, a chronic inflammatory disorder of unknown etiology associated with lymphadenopathy and subcutaneous masses in the head and neck region. He has had moderate-severe hypertriglyceridemia (200-1000 mg/dl) since age 25. Genetic testing (LPL, APOA5, APOC2, GPIHBP1) was negative.

Figure 8:
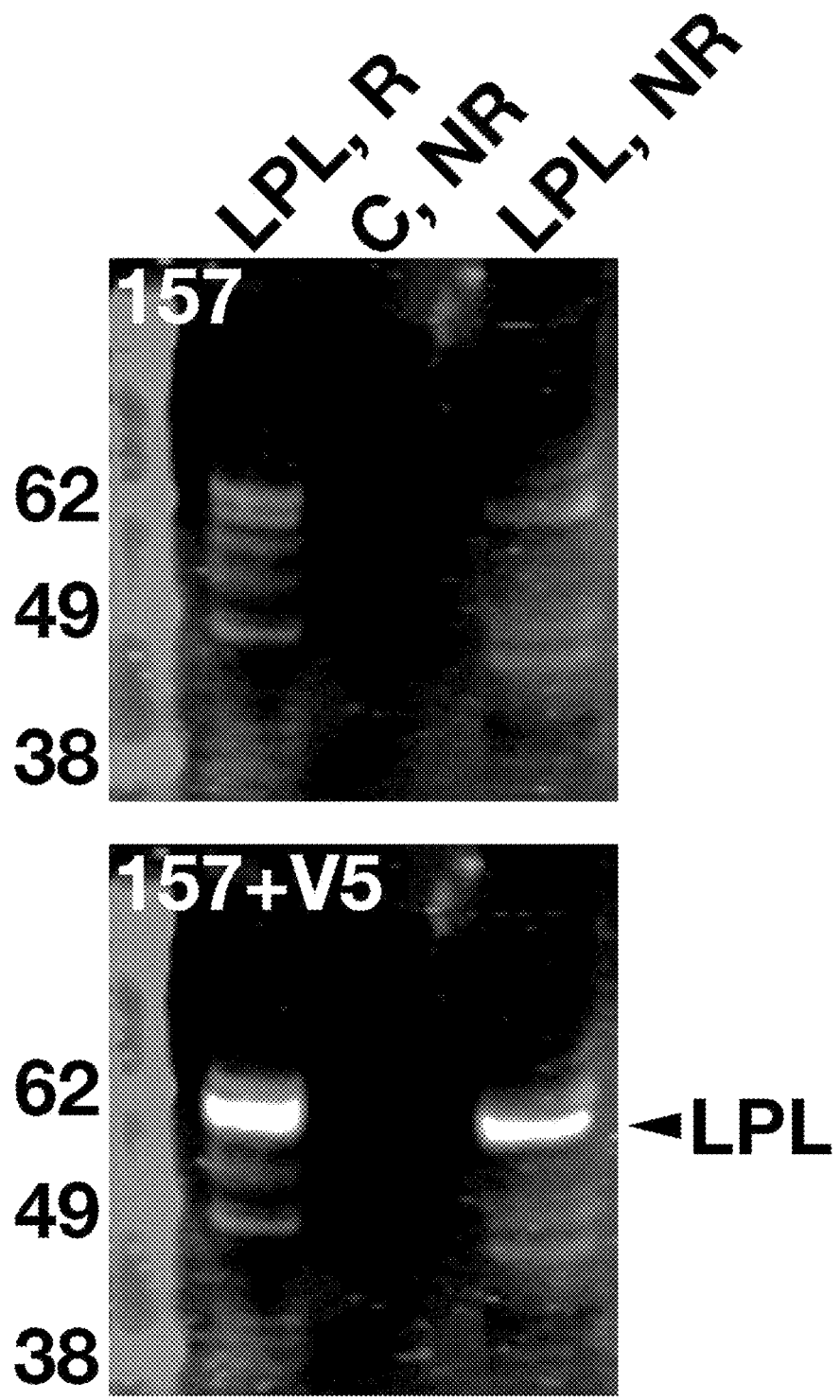
FIG. 8. Lack of evidence for LPL autoantibodies in plasma 157. V5-tagged human LPL (77 ng/lane) from CHO cells was separated by SDS-PAGE under reducing (R) and nonreducing (NR) conditions. Western blots were performed with plasma 157 (20 AU GPIHBP1 autoantibodies/ml) followed by an IRDye680-labeled goat anti-human IgG. Binding of IRDye800-labeled V5 antibody (lower panel, LPL) was also assessed. Immunoglobulins in plasma 157 bound nonspecifically to proteins with a molecular weight close to that of V5-LPL, but they did not detect the same band recognized by the V5 antibody. C, CHO cell medium. Plasma 157 also tested negative for LPL autoantibodies with an ELISA.

Patient 157, a 26-year-old female from South Africa has been described previously. She was referred at age 26 (September 2002) for new-onset hypertriglyceridemia and recurrent bouts of pancreatitis. She had a history of SLE. At the time of referral, she was positive for anti-dsDNA antibodies (75.4 μg/ml), and her fasting plasma triglyceride level was 2,407 mg/dl. The lipoprotein electrophoresis pattern suggested chylomicronemia, and there was virtually no LPL activity in the post-heparin plasma. A mixing experiment suggested the possibility of LPL autoantibodies. She was treated with 6 plasma exchanges and subsequently with cyclophosphamide and high-dose steroids, and the triglyceride levels normalized. One year later, she presented with recurrent hypertriglyceridemia and pancreatitis but did not respond to intensified immunosuppression and plasma exchanges. In March 2004, the patient was given rituximab (four weekly doses of 375 mg/m$^2$) along with cyclophosphamide and prednisone. The plasma triglycerides normalized, but the patient developed chronic abdominal pain (presumably related to chronic pancreatitis) and ultimately succumbed to an unrelated illness (Huntington's disease). As shown in FIG. 8, there was a lack of evidence for LPL autoantibodies in plasma 157.

Figure 9:
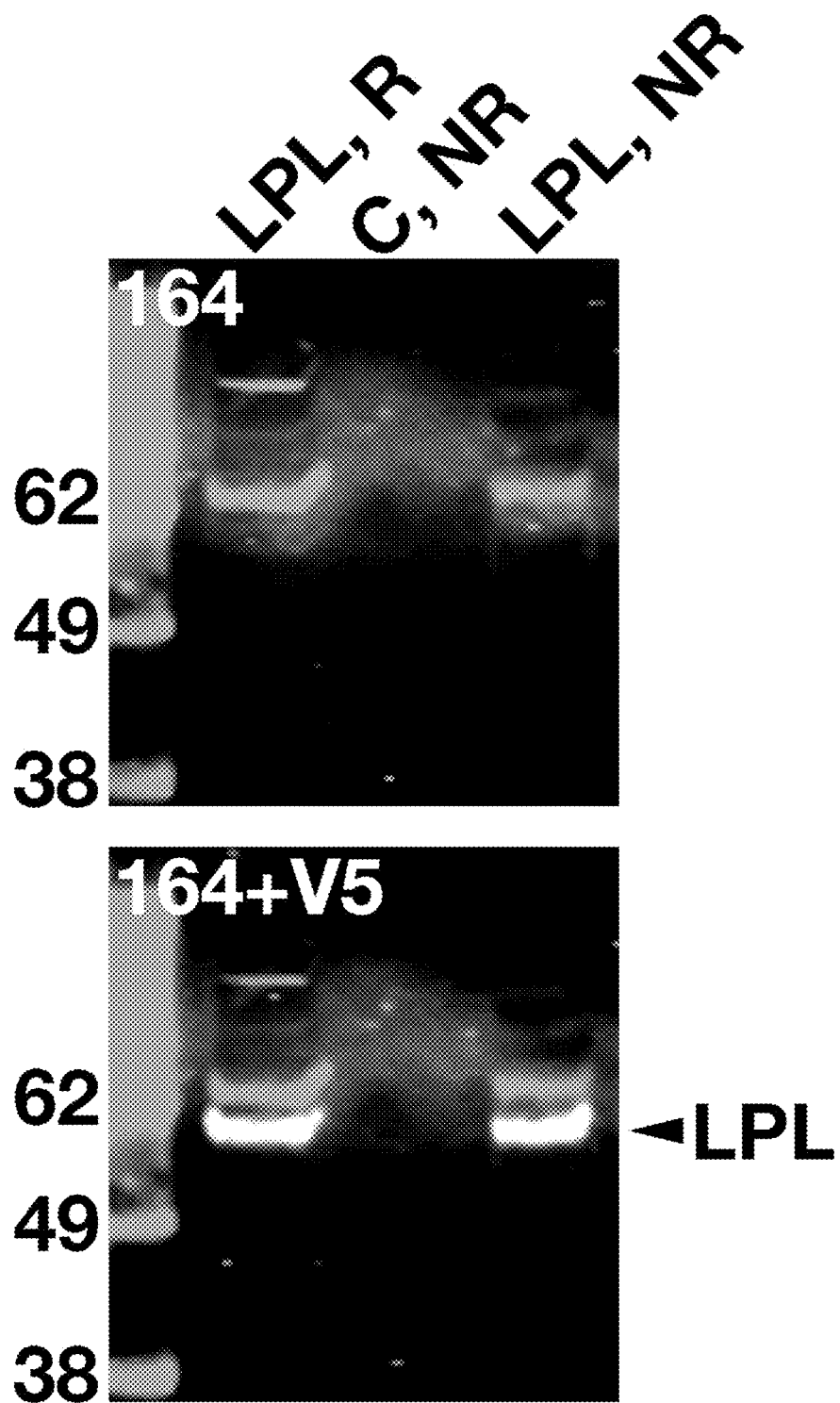
FIG. 9. Absence of LPL autoantibodies in plasma 164. Western blot analysis showing that the immunoglobulins in plasma 164 do not bind to reduced (R) or nonreduced (NR) V5-tagged recombinant human LPL (77 ng/lane). An IRDye800-labeled V5 antibody (lower panel, LPL) bound equally well to reduced and nonreduced LPL. Immunoglobulins in plasma 164 bound to a protein with a molecular weight close to that of V5-LPL, but they did not detect the same band recognized by the V5 antibody. C, CHO cell medium. Plasma 164 also tested negative for LPL autoantibodies with an ELISA.

Patient 164, a 9-year-old African-American girl, was previously described. She was initially referred for severe hypertriglyceridemia (4,784 mg/dl) and acute pancreatitis. She had been healthy until 6 weeks earlier, when she experienced abdominal pain and vomiting. She was treated with omega-3 acid ethyl esters, fenofibrate, and a low-fat diet. This regimen had little effect on the hypertriglyceridemia, but her serum triglyceride levels fell below 500 mg/dl on a very low fat diet. There was no family history of hypertriglyceridemia, pancreatitis, or consanguinity, and genetic testing excluded mutations in LPL, GPIHBP1, APOA5, APOC2, or LMF1. The authors of the initial report reported, on the basis of a western blot, that the subject had LPL autoantibodies. Her mother had SLE, and her maternal grandmother had multiple sclerosis. Patient 164 had two episodes of joint swelling (ankle, knee, and wrist) and tested positive for antinuclear and anti-cardiolipin antibodies. She tested weakly positive for Sjögren's syndrome antigen B (SS-B) and rheumatoid factor. She was negative for anti-dsDNA, anti-Smith, anti-ribonucleoprotein, and SS-A antibodies. Patient 164 was diagnosed with Sjögren's syndrome after a salivary gland biopsy revealed infiltration with lymphocytes and immunoblasts. She was placed on immunosuppressive therapy with prednisone (20 mg/day) and mycophenolate mofetil (500 mg twice daily). After increasing the dose of mycophenolate mofetil (750 mg in the morning and 500 mg in the evening) and gradually replacing prednisone with hydroxychloroquine (100 mg/day), the plasma triglyceride levels normalized (Table 2). As shown in FIG. 9, there was a lack of evidence for LPL autoantibodies in plasma 164.

Patient 102, a 38-year-old female native of the Philippines, was referred for severe hypertriglyceridemia. Post-heparin LPL activity levels in the plasma were less than 10% of normal, and a mixing experiment to test for LPL autoantibodies was negative. She had no mutations in LPL or GPIHBP1. She was diagnosed with SLE in 2013. We confirmed a high titer of antinuclear antibodies (ANA) in her plasma (Table 2). In 2015, the patient developed pancreatitis at week 33 of pregnancy and had plasma triglyceride levels of 6,500 mg/dl. She received plasmaphereses and was treated with hydrocortisone, prednisone, and vitamins. The delivery of a baby girl, patient 103, needed to be induced but was otherwise normal. Patient 102 was seen 1 month postpartum and was treated with a low-fat diet, fish oil, and 5 mg/day of prednisone.

Patient 103, the daughter of patient 102, was born with Agpar scores of 9/9 and weighed 1550 g. At birth the blood was lipemic; the plasma triglyceride levels on days 1 and 2 were 9,090 and 5,360 mg/dl, respectively. The blood sample from day 1 was positive for GPIHBP1 autoantibodies and antinuclear antibodies. She was placed on a medium chain triglyceride-rich formula (Enfaport) and was treated with ampicillin and gentamycin for possible sepsis. Her plasma triglyceride levels fell to 401 mg/dl after 10 days and to 114 mg/dl two weeks later. She was discharged on day 24 and weighed 1890 g. At 1 year of age, the plasma triglyceride levels were 72 mg/dl (Table 2).

F. Discussion

The inventors describe the discovery of autoantibodies against GPIHBP1, the protein that shuttles LPL to the capillary lumen, in the plasma of six patients with severe hypertriglyceridemia. This data provide strong support for the conclusion that the GPIHBP1 autoantibodies were the cause of the observed hypertriglyceridemia. First, the autoantibodies blocked the binding of GPIHBP1 to LPL. Second, the plasma levels of LPL were very low in the GPIHBP1 autoantibody patients, consistent with impaired transport of LPL to the capillary lumen. Third, immunosuppressive drug therapy normalized triglyceride levels in patients 157 and 164. Fourth, patient 102 delivered a baby (patient 103) who was born with GPIHBP1 autoantibodies. That infant had plasma triglyceride levels of 9,090 mg/dl on the first day of life, but the hyperlipidemia steadily waned, consistent with a gradual disappearance of maternal IgGs.

GPIHBP1 binds LPL in the interstitial spaces and transports it to the capillary lumen (FIG. 6(A)). GPIHBP1 is a long-lived protein that moves bidirectionally across capillary endothelial cells. In mouse models, GPIHBP1 has been shown to transport a GPIHBP1-specific monoclonal antibody from the capillary lumen to the basolateral surface of endothelial cells; GPIHBP1 transported the same monoclonal antibody from the interstitial spaces to the capillary lumen. In the GPIHBP1 autoantibody patients, the autoantibodies bind to GPIHBP1 in capillaries, and it is likely (given the antibody transport studies in mice) that the GPIHBP1-autoantibody complexes move back and forth across endothelial cells (FIGS. 6 (A and B)). Because GPIHBP1 autoantibodies abolish LPL binding, the inventors further assume that the transport of LPL to the capillary lumen in autoantibody patients is negligible and that the LPL is mislocalized in the interstitial spaces—as it is in GPIHBP1-deficient mice (FIG. 6(B)).

Previous studies have reported that chylomicronemia can be caused by autoantibodies against LPL. GPIHBP1 autoantibody patient 157 was suspected to have LPL autoantibodies, but none were found. The initial suspicion of LPL autoantibodies was based on spiking the patient's plasma into the post-heparin plasma of a normal participant and finding reduced amounts of triglyceride hydrolysis. This assay is problematic because of the inherent instability of LPL and competition from plasma lipoproteins. Also, patient 164 was reported to have LPL autoantibodies by western blot, but none were found, and in hindsight the initial western blot was not definitive.

Four of the six GPIHBP1 autoantibody patients with chylomicronemia carried diagnoses of autoimmune diseases (SLE or Sjögren's syndrome). These patients can develop autoantibodies against many proteins, and the data indicates that GPIHBP1 is one of these. Because of transfer of maternal autoantibodies, some infants born to mothers with SLE develop neonatal lupus (characterized by cutaneous lesions and cardiac conduction abnormalities). Based on this data, chylomicronemia is a potential finding in infants born to mothers with SLE. Importantly, two of the six GPIHBP1 autoantibody patients had no evidence of rheumatologic disease. Thus, it is believed that GPIHBP1 autoantibodies should be considered in patients with acquired chylomicronemia whether or not there are findings of autoimmune disease.

GPIHBP1 is one of ~25 Ly6 proteins, each characterized by one or more three-fingered Ly6 domain(s) containing 8 or 10 cysteines—all disulfide-bonded. The autoantibodies in the patients bound to properly folded GPIHBP1 monomers with intact disulfide bonds, and the autoantibodies did not cross-react with other Ly6 proteins, including CD59. It is intriguing that other autoantibodies associated with human disease bind to cysteine-rich domains in proteins. For example, autoantibodies against the cysteine-rich region of ADAMTS13 cause thrombotic thrombocytopenic purpura; autoantibodies against a cysteine-rich domain of the TSH receptor have been identified in Graves' disease; and autoantibodies against a cysteine-rich domain of the phospholipase A2 receptor (PLA2R) have been identified in membranous nephropathy.

In these studies, immunoassay interference was the clue that led to the identification of GPIHBP1 autoantibodies. Immunoassay interference from autoantibodies is well known to clinical chemists. For example, autoantibodies against troponin can interfere with troponin assays used to diagnose myocardial infarction, and autoantibodies against TSH, thyroxine, and triiodothyronine can interfere with immunoassays used to diagnose thyroid diseases.

In summary, the inventors identified autoantibodies against GPIHBP1 that block the ability of this protein to bind LPL and transport it from the interstitial space to the capillary lumen. These autoantibodies, identified in six patients, interfered with LPL-mediated processing of triglyceride-rich lipoproteins and caused severe hypertriglyceridemia.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references, scientific publications, and patent publications are specifically incorporated by reference for all purposes.

REFERENCES

1. Beigneux A P, Davies B, Gin P, et al. Glycosylphosphatidylinositol-anchored high density lipoprotein-binding protein 1 plays a critical role in the lipolytic processing of chylomicrons. Cell Metab 2007; 5:279-91.
2. Davies B S, Beigneux A P, Barnes R H, 2nd, et al. GPIHBP1 is responsible for the entry of lipoprotein lipase into capillaries. Cell Metab 2010; 12:42-52.
3. Franssen R, Young S G, Peelman F, et al. Chylomicronemia with low postheparin lipoprotein lipase levels in the setting of GPIHBP1 defects. Circ Cardiovasc Genet 2010; 3:169-78.
4. Olivecrona G, Ehrenborg E, Semb H, et al. Mutation of conserved cysteines in the Ly6 domain of GPIHBP1 in familial chylomicronemia. J Lipid Res 2010; 51:1535-45.
5. Charrière S, Peretti N, Bernard S, et al. GPIHBP1 C89F neomutation and hydrophobic C-terminal domain G175R mutation in two pedigrees with severe hyperchylomicronemia. J Clin Endocrinol Metab 2011; 96:E1675-E9.
6. Coca-Prieto I, Kroupa O, Gonzalez-Santos P, et al. Childhood-onset chylomicronaemia with reduced plasma lipoprotein lipase activity and mass: identification of a novel GPIHBP1 mutation. J Intern Med 2011; 270:224-8.
7. Rios J J, Shastry S, Jasso J, et al. Deletion of GPIHBP1 causing severe chylomicronemia. J Inherit Metab Dis 2012; 35:531-40.
8. Beigneux A P, Fong L G, Bensadoun A, et al. GPIHBP1 missense mutations often cause multimerization of GPIHBP1 and thereby prevent Lipoprotein Lipase binding. Circ Res 2014; 116:624-32.
9. Plengpanich W, Young S G, Khovidhunkit W, et al. Multimerization of GPIHBP1 and familial chylomicronemia from a serine-to-cysteine substitution in GPIHBP1's Ly6 domain. J Biol Chem 2014; 289:19491-9.
10. Hu X, Sleeman M, Miyashita K, et al. Monoclonal antibodies that bind to the Ly6 domain of GPIHBP1 abolish the binding of LPL. J Lipid Res 2017; 58:208-15.
11. Machida T, Miyashita K, Sone T, et al. Determination of serum lipoprotein lipase using a latex particle-enhanced turbidimetric immunoassay with an automated analyzer. Clin Chim Acta 2015; 442:130-5.
12. Young S G, Smith R S, Hogle D M, Curtiss L K, Witztum J L. Two new monoclonal antibody-based enzyme-linked assays of apolipoprotein B. Clin Chem 1986; 32:1484-90.
13. Beigneux A P, Davies B S J, Tat S, et al. Assessing the role of the glycosylphosphatidylinositol-anchored high density lipoprotein-binding protein 1 (GPIHBP1) three-finger domain in binding lipoprotein lipase. J Biol Chem 2011; 286:19735-43.
14. Blom D J, Marais A D. Severe hypertriglyceridemia in a patient with lupus. Am J Med 2005; 118:443-4.
15. Ashraf A P, Beukelman T, Pruneta-Deloche V, Kelly D R, Garg A. Type 1 hyperlipoproteinemia and recurrent acute pancreatitis due to lipoprotein lipase antibody in a young girl with Sjögren's syndrome. J Clin Endocrinol Metab 2011; 96:3302-7.
16. Olafsen T, Young S G, Davies B S J, et al. Unexpected expression pattern for glycosylphosphatidylinositol-anchored HDL-binding protein 1 (GPIHBP1) in mouse tissues revealed by positron emission tomography scanning. J Biol Chem 2010; 285:39239-48.
17. Davies B S, Goulbourne C N, Barnes R H, 2nd, et al. Assessing mechanisms of GPIHBP1 and lipoprotein lipase movement across endothelial cells. J Lipid Res 2012; 53:2690-7.
18. Pruneta V, Moulin P, Labrousse F, Bondon P J, Ponsin G, Berthezene F. Characterization of a new case of autoimmune type I hyperlipidemia: long-term remission under immunosuppressive therapy. J Clin Endocrinol Metab 1997; 82:791-6.
19. Yoshimura T, Ito M, Sakoda Y, Kobori S, Okamura H. Rare case of autoimmune hyperchylomicronemia during pregnancy. Eur J Obstet Gynecol Reprod Biol 1998; 76:49-51.
20. Kihara S, Matsuzawa Y, Kubo M, et al. Autoimmune hyperchylomicronemia. N Engl J Med 1989; 320:1255-9.
21. Pruneta-Deloche V, Marcais C, Perrot L, et al. Combination of circulating antilipoprotein lipase (Anti-LPL) antibody and heterozygous 5172 fsX179 mutation of LPL gene leading to chronic hyperchylomicronemia. J Clin Endocrinol Metab 2005; 90:3995-8.
22. Izmirly P M, Llanos C, Lee L A, Askanase A, Kim M Y, Buyon J P. Cutaneous manifestations of neonatal lupus and risk of subsequent congenital heart block. Arthritis Rheum 2010; 62:1153-7.
23. Ostertag E M, Kacir S, Thiboutot M, et al. ADAMTS13 autoantibodies cloned from patients with acquired thrombotic thrombocytopenic purpura: 1. Structural and functional characterization in vitro. Transfusion 2016; 56:1763-74.
24. Chen C R, Tanaka K, Chazenbalk G D, McLachlan S M, Rapoport B. A full biological response to autoantibodies in Graves' disease requires a disulfide-bonded loop in the thyrotropin receptor N terminus homologous to a laminin epidermal growth factor-like domain. J Biol Chem 2001; 276:14767-72.
25. Schwarz-Lauer L, Pichurin P N, Chen C R, et al. The cysteine-rich amino terminus of the thyrotropin receptor is the immunodominant linear antibody epitope in mice immunized using naked deoxyribonucleic acid or adenovirus vectors. Endocrinology 2003; 144:1718-25.
26. Hamidi S, Chen C R, Murali R, McLachlan S M, Rapoport B. Probing structural variability at the N terminus of the TSH receptor with a murine monoclonal antibody that distinguishes between two receptor conformational forms. Endocrinology 2013; 154:562-71.
27. Fresquet M, Jowitt T A, Gummadova J, et al. Identification of a major epitope recognized by PLA2R autoantibodies in primary membranous nephropathy. J Am Soc Nephrol 2015; 26:302-13.
28. Eriksson S, Hellman J, Pettersson K. Autoantibodies against cardiac troponins. N Engl J Med 2005; 352:98-100.
29. Despres N, Grant A M. Antibody interference in thyroid assays: a potential for clinical misinformation. Clin Chem 1998; 44:440-54.
30. Gardsvoll H, Hansen L V, Jorgensen T J, Ploug M. A new tagging system for production of recombinant proteins in *Drosophila* S2 cells using the third domain of the urokinase receptor. Protein Expr Purif 2007; 52:384-94.

What is claimed is:

1. A method for detecting GPIHBP1 autoantibodies in a plasma or serum sample from a human subject, the method comprising:
   a. contacting the plasma or serum sample with a GPIHBP1 polypeptide; and
   b. detecting the presence or absence of binding of the GPIHBP1 polypeptide and GPIHBP1 autoantibodies in the plasma or serum sample from step (a).

2. The method of claim 1, wherein detecting the presence or absence of binding comprises an ELISA assay.

3. The method of claim 1, wherein the GPIHBP1 polypeptide is recombinant.

4. The method of claim 3, wherein the recombinant GPIHBP1 polypeptide comprises an amino acid sequence with at least 80% identity to SEQ ID NO:4.

5. The method of claim 1, wherein the GPIHBP1 polypeptide is monomeric non-reduced GPIHBP1.

6. The method of claim 1, wherein the subject has been diagnosed with hypertriglyceridemia.

7. The method of claim 1, wherein the subject is not genetically deficient for GPIHBP1.

8. The method of claim 1, wherein the detected autoantibodies comprise autoantibodies that bind specifically to monomeric non-reduced GPIHBP1.

9. The method of claim 1, wherein the method further comprises isolating GPIHBP1 autoantibodies from the subject.

10. The method of any claim 9, wherein the method further comprises detecting the binding of LPL to GPIHBP1 in the presence of the autoantibodies.

11. The method of claim 1, wherein the method further comprises contacting the sample with LPL and detecting the binding between LPL and the GPIHBP1 polypeptide in the presence of the sample from the subject.

12. The method of claim 1, wherein the subject does not have diabetes, does not have coronary artery disease, is not obese, and/or wherein the patient is one that has been determined to have low levels of LPL in a sample from the subject compared to a control.

13. The method of claim 1, wherein the method further comprises detecting the level of LPL in a sample from the subject.

* * * * *

SEQUENCE LISTING

<160> NUMBER OF SEQ ID NOS: 5

<210> SEQ ID NO 1
<211> LENGTH: 184
<212> TYPE: PRT
<213> ORGANISM: Homo sapiens

<400> SEQUENCE: 1

```
Met Lys Ala Leu Gly Ala Val Leu Leu Ala Leu Leu Leu Phe Gly Arg
 1               5                  10                  15

Pro Gly Arg Gly Gln Thr Gln Gln Glu Glu Glu Glu Glu Asp Glu Asp
            20                  25                  30
```

```
His Gly Pro Asp Asp Tyr Asp Glu Glu Asp Glu Asp Glu Val Glu Glu
            35                  40                  45

Glu Glu Thr Asn Arg Leu Pro Gly Gly Arg Ser Arg Val Leu Leu Arg
 50                  55                  60

Cys Tyr Thr Cys Lys Ser Leu Pro Arg Asp Glu Arg Cys Asn Leu Thr
 65                  70                  75                  80

Gln Asn Cys Ser His Gly Gln Thr Cys Thr Thr Leu Ile Ala His Gly
                 85                  90                  95

Asn Thr Glu Ser Gly Leu Leu Thr Thr His Ser Thr Trp Cys Thr Asp
                100                 105                 110

Ser Cys Gln Pro Ile Thr Lys Thr Val Glu Gly Thr Gln Val Thr Met
            115                 120                 125

Thr Cys Cys Gln Ser Ser Leu Cys Asn Val Pro Pro Trp Gln Ser Ser
130                 135                 140

Arg Val Gln Asp Pro Thr Gly Lys Gly Ala Gly Gly Pro Arg Gly Ser
145                 150                 155                 160

Ser Glu Thr Val Gly Ala Ala Leu Leu Asn Leu Leu Ala Gly Leu
                165                 170                 175

Gly Ala Met Gly Ala Arg Arg Pro
            180

<210> SEQ ID NO 2
<211> LENGTH: 125
<212> TYPE: PRT
<213> ORGANISM: Homo sapiens

<400> SEQUENCE: 2

Met Lys Ala Leu Gly Ala Val Leu Leu Ala Leu Leu Leu Phe Gly Arg
 1               5                  10                  15

Pro Gly Arg Gly Gln Thr Gln Gln Glu Glu Glu Glu Asp Glu Asp
            20                  25                  30

His Gly Pro Asp Asp Tyr Asp Glu Glu Asp Glu Asp Glu Val Glu Glu
            35                  40                  45

Glu Glu Thr Asn Arg Leu Pro Gly Gly Arg Ser Arg Val Leu Leu Arg
 50                  55                  60

Cys Tyr Thr Cys Lys Ser Leu Pro Arg Asp Glu Arg Cys Asn Leu Thr
 65                  70                  75                  80

Gln Asn Cys Ser His Gly Gln Thr Cys Thr Thr Leu Ile Ala His Gly
                 85                  90                  95

Asn Thr Glu Ser Gly Leu Leu Thr Thr His Ser Thr Trp Cys Thr Asp
                100                 105                 110

Ser Cys Gln Pro Ile Thr Lys Thr Val Glu Gly Thr Gln
            115                 120                 125

<210> SEQ ID NO 3
<211> LENGTH: 834
<212> TYPE: DNA
<213> ORGANISM: Homo sapiens

<400> SEQUENCE: 3
cgccagtgtt acagctgcaa ggggaacagc acccatggat gctcctctga agagactttc      60
ctcattgact gccgaggccc catgaatcaa tgtctggtag ccaccggcac tcacgaaccg     120
aaaaaccaaa gctatatggt aagaggctgt gcaaccgcct caatgtgcca acatgcccac     180
ctgggtgacg ccttcagcat gaaccacatt gatgtctcct gctgtactaa agtggctgt     240 aaccacccag acctggatgt ccagtaccgc agtgggctcg aggacgacga cgataagcag     300
```

```
acacagcagg aggaagagga agaggacgag gaccacgggc cagatgacta cgacgaggaa    360
gatgaggatg aggtggaaga ggaggagacc aacaggctcc ctggtggcag gagcagagtg    420
ctgctgcggt gctacacctg caagtccctg cccagggacg agcgctgcaa cctgacgcag    480
aactgctcac atggccagac ctgcacaacc ctcattgccc acgggaacac cgagtcaggc    540
ctcctgacca cccactccac gtggtgcaca gacagctgcc agcccatcac caagacggtg    600 gagggggaccc aggtgaccat gacctgctgc cagtccagcc tgtgcaatat tccaccctgg    660
cagaaccccc aagtccagaa ccctctgggt ggccgggcag acagccccct ggaaagtggg    720
actagacatc ctcagggtgg caagtttagc caccccagg ttgtcaaggc tgctcatcct    780
cagagcgatg gggctaactt gcctaagagt ggcaaggcta accagcccca gtga           834
```

<210> SEQ ID NO 4
<211> LENGTH: 277
<212> TYPE: PRT
<213> ORGANISM: Homo sapiens

<400> SEQUENCE: 4

```
Arg Gln Cys Tyr Ser Cys Lys Gly Asn Ser Thr His Gly Cys Ser Ser
1               5                   10                  15

Glu Glu Thr Phe Leu Ile Asp Cys Arg Gly Pro Met Asn Gln Cys Leu
            20                  25                  30

Val Ala Thr Gly Thr His Glu Pro Lys Asn Gln Ser Tyr Met Val Arg
        35                  40                  45

Gly Cys Ala Thr Ala Ser Met Cys Gln His Ala His Leu Gly Asp Ala
    50                  55                  60

Phe Ser Met Asn His Ile Asp Val Ser Cys Cys Thr Lys Ser Gly Cys
65                  70                  75                  80

Asn His Pro Asp Leu Asp Val Gln Tyr Arg Ser Gly Leu Glu Asp Asp
                85                  90                  95

Asp Asp Lys Gln Thr Gln Gln Glu Glu Glu Glu Asp Glu Asp His
            100                 105                 110

Gly Pro Asp Asp Tyr Asp Glu Glu Asp Glu Asp Glu Val Glu Glu Glu
        115                 120                 125

Glu Thr Asn Arg Leu Pro Gly Gly Arg Ser Arg Val Leu Leu Arg Cys
    130                 135                 140

Tyr Thr Cys Lys Ser Leu Pro Arg Asp Glu Arg Cys Asn Leu Thr Gln
145                 150                 155                 160

Asn Cys Ser His Gly Gln Thr Cys Thr Thr Leu Ile Ala His Gly Asn
                165                 170                 175

Thr Glu Ser Gly Leu Leu Thr Thr His Ser Thr Trp Cys Thr Asp Ser
            180                 185                 190

Cys Gln Pro Ile Thr Lys Thr Val Glu Gly Thr Gln Val Thr Met Thr
        195                 200                 205

Cys Cys Gln Ser Ser Leu Cys Asn Ile Pro Pro Trp Gln Asn Pro Gln
    210                 215                 220

Val Gln Asn Pro Leu Gly Gly Arg Ala Asp Ser Pro Leu Glu Ser Gly
225                 230                 235                 240

Thr Arg His Pro Gln Gly Gly Lys Phe Ser His Pro Gln Val Val Lys
                245                 250                 255

Ala Ala His Pro Gln Ser Asp Gly Ala Asn Leu Pro Lys Ser Gly Lys
            260                 265                 270

Ala Asn Gln Pro Gln
```

-continued

<210> SEQ ID NO 5
<211> LENGTH: 475
<212> TYPE: PRT
<213> ORGANISM: Homo sapiens

<400> SEQUENCE: 5

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
        115                 120                 125

Lys Leu Val Gly Gln Asp Val Ala Arg Phe Ile Asn Trp Met Glu Glu
130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
        195                 200                 205

Leu His Thr Phe Thr Arg Gly Ser Pro Gly Arg Ser Ile Gly Ile Gln
    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

-continued

```
Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Met Leu Lys Leu Lys Trp Lys Ser Asp Ser Tyr Phe Ser
            405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
        435                 440                 445

Lys Val Ser His Leu Gln Lys Gly Lys Ala Pro Ala Val Phe Val Lys
    450                 455                 460

Cys His Asp Lys Ser Leu Asn Lys Lys Ser Gly
465                 470                 475
```